US008124107B2

(12) United States Patent
Hook et al.

(10) Patent No.: US 8,124,107 B2
(45) Date of Patent: Feb. 28, 2012

(54) ANTIBODIES RECOGNIZING A HIGHLY EXPRESSED PUTATIVE ANTIGEN OF CA-MRSA AND METHODS OF USE

(75) Inventors: Magnus Hook, Houston, TX (US); Maria Labandeira-Rey, Irving, TX (US); Gabriela M. Bowden, Sugar Land, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 12/279,079

(22) PCT Filed: Feb. 22, 2007

(86) PCT No.: PCT/US2007/004497
§ 371 (c)(1),
(2), (4) Date: Nov. 24, 2008

(87) PCT Pub. No.: WO2007/100580
PCT Pub. Date: Sep. 7, 2007

(65) Prior Publication Data
US 2009/0130115 A1    May 21, 2009

(51) Int. Cl.
    *A61K 39/00*    (2006.01)
    *A61K 39/38*    (2006.01)
    *A61K 39/02*    (2006.01)
    *A61K 39/085*   (2006.01)
    *A61K 39/09*    (2006.01)
(52) U.S. Cl. ............... 424/243.1; 424/190.1; 424/235.1; 424/236.1; 424/237.1; 530/350
(58) Field of Classification Search .................. None
    See application file for complete search history.

(56) References Cited

U.S. PATENT DOCUMENTS

| | | | |
|---|---|---|---|
| 3,867,517 A | 2/1975 | Ling | |
| 4,012,294 A | 3/1977 | Lossi et al. | |
| 4,098,876 A | 7/1978 | Piasio et al. | |
| 4,376,110 A | 3/1983 | David et al. | |
| 5,980,908 A * | 11/1999 | Hook et al. | 424/243.1 |
| 6,008,341 A | 12/1999 | Foster et al. | |
| 6,177,084 B1 | 1/2001 | Foster et al. | |
| 6,288,214 B1 | 9/2001 | Hook et al. | |
| 6,593,114 B1 * | 7/2003 | Kunsch et al. | 435/91.41 |
| 6,635,473 B1 | 10/2003 | Foster et al. | |
| 6,680,195 B1 | 1/2004 | Patti et al. | |
| 6,685,943 B1 | 2/2004 | Hook et al. | |
| 6,692,739 B1 | 2/2004 | Patti et al. | |
| 6,703,025 B1 | 3/2004 | Patti et al. | |
| 6,737,248 B2 * | 5/2004 | Kunsch et al. | 435/69.1 |
| 6,841,154 B2 | 1/2005 | Foster et al. | |
| 6,979,446 B2 | 12/2005 | Patti et al. | |
| 6,994,855 B1 | 2/2006 | Foster et al. | |
| 7,045,131 B2 | 5/2006 | Patti et al. | |
| 7,855,272 B2 * | 12/2010 | Patti et al. | 530/350 |
| 7,968,100 B2 * | 6/2011 | Foster et al. | 424/190.1 |
| 8,007,803 B2 * | 8/2011 | Emery et al. | 424/165.1 |
| 8,007,811 B2 * | 8/2011 | Emery et al. | 424/190.1 |
| 8,017,133 B2 * | 9/2011 | Patti et al. | 424/243.1 |
| 2003/0054436 A1 * | 3/2003 | Kunsch et al. | 435/69.1 |
| 2004/0043037 A1 * | 3/2004 | Kunsch et al. | 424/190.1 |
| 2006/0115490 A1 * | 6/2006 | Masignani et al. | 424/190.1 |
| 2007/0020746 A1 * | 1/2007 | Kunsch et al. | 435/252.3 |
| 2007/0031850 A1 * | 2/2007 | Mounts et al. | 435/6 |
| 2009/0074755 A1 * | 3/2009 | Taylor et al. | 424/133.1 |
| 2009/0130115 A1 * | 5/2009 | Hook et al. | 424/139.1 |
| 2009/0269396 A1 * | 10/2009 | Cipolla et al. | 424/450 |
| 2011/0150918 A1 * | 6/2011 | Foster et al. | 424/190.1 |
| 2011/0171285 A1 * | 7/2011 | Hook et al. | 424/447 |

FOREIGN PATENT DOCUMENTS

| | | |
|---|---|---|
| WO | WO 02/094868 A2 * | 11/2002 |
| WO | WO 2007/100580 A2 * | 9/2007 |
| WO | WO 2007/145689 * | 12/2007 |

OTHER PUBLICATIONS

Holden et al, PNAS, Jun. 29, 2004, 101/26:9786-9791.*
Herron-Olson et al, PLoS One, 2007, 2:E1120-E1120.*
Projan et al, Current Opinion in Pharmacology, 2006, 6:473-479.*
Creech et al, Vaccine, 2010, 28:256-260.*
Schaffer et al, International J. Antimicrobial Agents, 2008, 325:571-578.*
Easton et al, J. Hospital Infection, 2007, 66:29-33.*
Holden e tal, PNAS, USA, Jun. 29, 2004, 101/26:9786-9791.*
Baba et al, Lancet, 2002, 359:1819-1827.*
Habeck, The Lancet, Infectious Diseases, Apr. 2002, 2:201.*
Gleeson, Dis. Mon., Dec. 2008, 54:801-806.*
Joh et al, Matrix Biology, 1999, 18:211-223.*
Rivas et al, Current Opinion in Drug Discovery and Development, 2004, 7/2:223-227.*
Brown et al, Clin. Microbiol. Infect., Feb. 2009, 15/2:156-164.*
Foster et al, TRENDS in Microbiology, Dec. 1998, 6/12:484-488.*
Patti, Vaccine, 2004, 22S:S39-S43.*
Kupferwasser et al, Abstracts of General Meeting of ASM, 2003, 103:D241 abstract only.*
Patti et al, Annual Review of Microbiology, 1994, 48:585-617.*
Hook et al, Zentralblatt fuer Bakteriologie, Supplement (1994), 27 (Molecular Pathogenesis of Surgical Infections):134-144.*
Holden, M.T.G., "Complete genomes of two clinical *Staphylococcus areus* strains; Evidence for the rapid evolution of virulence and drug resistance", Jun. 29, 2004, pp. 9786-9791, vol. 101, No. 26, PNAS.
Baba, T., "Genome and virulence determinants of high virulence community-acquired MRSA" 2002, pp. 1819-1827, vol. 359, The Lancet.
Kuroda, M. "Whole genome sequencing of metticillin-resistant *Staphylococcus areus*", 2001, pp. 1225-1240, vol. 357, The Lancet.
Database UniProt [Online] Oct. 1, 2002, Baba, T. et al, "Putative uncharacterized protein MW0118 from *Staphylococcus aureus*" XP002594307, Database accession No. Q8NYQ7 Aa sequence.
Database UniProt [Online] Jul. 10, 2004, Holden, M.T.G. et al, "Putative exported protein SAS0118 from *Staphylococcus aureus*", XP002594308, Database accession No. Q6GCY0 Aa sequence.
Rivas, Jorge M. et al, "MSCRAMM-Targeted Vaccines and Immunotherapy for Staphylococcal Infection", Mar. 1, 2004, pp. 223-227, vol. 7, No. 2, Current Opinion in Drug Discovery and Development, Current Drugs, London, Great Britain.

* cited by examiner

*Primary Examiner* — Nita M Minnifield

(74) *Attorney, Agent, or Firm* — B. Aaron Schulman, Esq.; Terry L. Wright, Esq.; Stites & Harbison PLLC

(57) ABSTRACT

The present invention provides MSCRAMM® proteins from *S. aureus* which are putative highly-expressed antigens from methicillin-resistant *S. aureus*, including communit-associated MRSA (CA-MRSA), and these antigens can thus be utilized in methods of generating antibodies capable of binding these antigens which can be useful in methods of treating or preventing infection from MRSA. The present invention is directed to these proteins, antibodies capable of binding these proteins, methods of generating said antibodies, nucleic acids coding for said proteins, and pharmaceutical compositions or vaccines which include the proteins or antibodies of the present invention in combination with a pharmaceutically acceptable vehicle, carrier or excipient.

5 Claims, 6 Drawing Sheets

Figure 1. a. Cell wall protein extraction. b. Western blot analysis using monoclonal anti-Spa IgG. c. Western blot analysis using anti-SdrD polyclonal IgG. Lane 1: (PVL-negative/φSLT-negative), lane 2: PVL-negative/φSLT-positive, lane 3: PVL-positive/φSLT-positive.

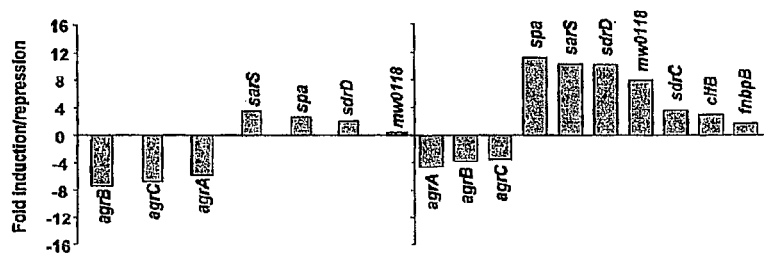

Figure 2. Fold decrease/increase levels of transcript from selected genes. Total RNA extracted from cultures grown at exponential (a) or stationary phase (b). Genes were considered to be induced or repressed in the PVL-positive strain if they were transcribed at least three fold higher/lower than in the PVL-negative strain. The shown transcripts encode: *agr A-C*, accessory regulator system; *sarS*, staphylococcal regulator S; *spa*, staphylococcal protein A; *sdrD and C*, serine aspartate proteins D and C; *mw0118*, putative cell-wall anchored protein; *clfB*, clumping factor B; *fnbpB*, fibronectin binding protein B.

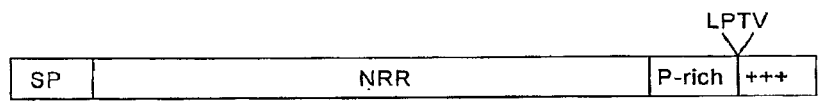
Figure 3. Schematic representation of MW0118. Sequence analysis and modeling programs predict a secretion signal (SS) and a non-repeated region (NRR) followed by a proline rich region. At the N-terminus, MW0118 contains a putative sortase recognition sequence for anchoring to the cell wall (LPTV) and a highly charged transmembrane domain.

Formatted Alignments

|  | 10 | 20 | 30 |
|---|---|---|---|
| SAUSA300_146 (Strain USA300) | M K K I Y K S L T V S A I V A T V S L S A L P Q S L A I T H |
| SACOL0129 (Strain COL) | M K K I Y K S L T V S A I V A T V S L S A L P Q S L A I T H |
| SAB0085 (Strain RF122) | M K K I Y K S L T V S V I V A T V S L S A L P Q S L A I T H |
| SAR0146 (Strain MRSA252) | M K N I Y K S L T V S A I V A T V S L S A L P Q S L A I T H |
| SAV0144 (Strain Mu50) | M K K I Y K S L T V S A I V A T V S L S A L P Q S L A I T H |
| SA0139 (Strain N315) | M K K I Y K S L T V S A I V A T V S L S A L P Q S L A I T H |
| SAS0118 (Strain MSSA476) | M K K I Y K S L T V S A I V A T V S L S A L P Q S L A I T H |
| MW0118 (Strain MW2) | M K K I Y K S L T V S A I V A T V S L S A L P Q S L A I T H |
|  | M K K I Y K S L T V S A I V A T V S L S A L P Q S L A I T H |

|  | 40 | 50 | 60 |
|---|---|---|---|
| SAUSA300_146 (Strain USA300) | E S Q P T K Q Q R T V L F D R S H G Q T A G A A D W V S D G |
| SACOL0129 (Strain COL) | E S Q P T K Q Q R T V L F D R S H G Q T A G A A D W V S D G |
| SAB0085 (Strain RF122) | E S Q P T K Q Q R T V L F D R S H G Q T A G A A D W V S D G |
| SAR0146 (Strain MRSA252) | E S Q P T K Q Q Q T V L F D R S H G Q T A G A A D W V S D G |
| SAV0144 (Strain Mu50) | E S Q P T K Q Q R T V L F D R S H G Q T A G A A D W V S D G |
| SA0139 (Strain N315) | E S Q P T K Q Q R T V L F D R S H G Q T A G A A D W V S D G |
| SAS0118 (Strain MSSA476) | E S Q P T K Q Q R T V L F D R S H G Q T A G A A D W V S D G |
| MW0118 (Strain MW2) | E S Q P T K Q Q R T V L F D R S H G Q T A G A A D W V S D G |
|  | E S Q P T K Q Q R T V L F D R S H G Q T A G A A D W V S D G |

|  | 70 | 80 | 90 |
|---|---|---|---|
| SAUSA300_146 (Strain USA300) | A F S D Y A D S I Q K Q G Y D V K A I D G H S N I T E A S L |
| SACOL0129 (Strain COL) | A F S D Y A D S I Q K Q G Y D V K A I D G H S N I T E A S L |
| SAB0085 (Strain RF122) | A F S D Y A D S I Q K Q G Y D V K A I D G H S N I T E A S L |
| SAR0146 (Strain MRSA252) | A F S D Y A D S I Q K Q G Y D V K A I D G H S N I T E A S L |
| SAV0144 (Strain Mu50) | A F S D Y A D S I Q K Q G Y D V K A I D G H S N I T E A S L |
| SA0139 (Strain N315) | A F S D Y A D S I Q K Q G Y D V K A I D G H S N I T E A S L |
| SAS0118 (Strain MSSA476) | A F S D Y A D S I Q K Q G Y D V K A I D G H S N I T E A S L |
| MW0118 (Strain MW2) | A F S D Y A D S I Q K Q G Y D V K A I D G H S N I T E A S L |
|  | A F S D Y A D S I Q K Q G Y D V K A I D G H S N I T E A S L |

|  | 100 | 110 | 120 |
|---|---|---|---|
| SAUSA300_146 (Strain USA300) | K S S K I F V I P E A N I P F K E S E Q A A I V K Y V K Q G |
| SACOL0129 (Strain COL) | K S S K I F V I P E A N I P F K E S E Q A A I V K Y V K Q G |
| SAB0085 (Strain RF122) | K S S K I F V I P E A N I P F K E S E Q A A I V N Y V K Q G |
| SAR0146 (Strain MRSA252) | K S S K I F V I P E A N I P F K E S E Q A A I V N Y V K Q G |
| SAV0144 (Strain Mu50) | K S S K I F V I P E A N I P F K E S E Q A A I Y N Y V K Q G |
| SA0139 (Strain N315) | K S S K I F V I P E A N I P F K E S E Q A A I V N Y V K Q G |
| SAS0118 (Strain MSSA476) | K S S K I F V I P E A N I P F K E S E Q A A I Y N Y V K Q G |
| MW0118 (Strain MW2) | K S S K I F V I P E A N I P F K E S E Q A A I Y N Y V K Q G |
|  | K S S K I F V I P E A N I P F K E S E Q A A I V N Y V K Q G |

|  | 130 | 140 | 150 |
|---|---|---|---|
| SAUSA300_146 (Strain USA300) | G N V V F I S D H Y N A D R N L N R I D S S E A M N G Y R R |
| SACOL0129 (Strain COL) | G N V V F I S D H Y N A D R N L N R I D S S E A M N G Y R R |
| SAB0085 (Strain RF122) | G N V V F I S D H Y N A D R N L N R I D S S E A M N G Y R R |
| SAR0146 (Strain MRSA252) | G N V V F I S D H Y N A D R N L N R I D S S E A M N G Y R R |
| SAV0144 (Strain Mu50) | G N V V F I S D H Y N A D R N L N R I D S S E A M N G Y R R |
| SA0139 (Strain N315) | G N V V F I S D H Y N A D R N L N R I D S S E A M N G Y R R |
| SAS0118 (Strain MSSA476) | G N V V F I S D H Y N A D R N L N R I D S S E A M N G Y R R |
| MW0118 (Strain MW2) | G N V V F I S D H Y N A D R N L N R I D S S E A M N G Y R R |
|  | G N V V F I S D H Y N A D R N L N R I D S S E A M N G Y R R |

|  | 160 | 170 | 180 |
|---|---|---|---|
| SAUSA300_146 (Strain USA300) | G A Y E D M S K G M N A E E K S S T A M Q G V K S S D W L S |
| SACOL0129 (Strain COL) | G A Y E D M S K G M N A E E K S S T A M Q G V K S S D W L S |
| SAB0085 (Strain RF122) | G A Y E D M S K G M N A E E K S S T A M Q G V K S S D W L S |
| SAR0146 (Strain MRSA252) | G A Y E D M S K G M N A E E K S S T A M Q G V K S S D W L S |
| SAV0144 (Strain Mu50) | G A Y E D M S K G M N A E E K S S T A M Q G V K S S D W L S |
| SA0139 (Strain N315) | G A Y E D M S K G M N A E E K S S T A M Q G V K S S D W L S |
| SAS0118 (Strain MSSA476) | G A Y E D M S K G M N A E E K S S T A M Q G V K S S D W L S |
| MW0118 (Strain MW2) | G A Y E D M S K G M N A E E K S S T A M Q G V K S S D W L S |
|  | G A Y E D M S K G M N A E E K S S T A M Q G V K S S D W L S |

FIG. 4 A

```
                                        190                 200                 210
SAUSA300_146 (Strain USA300)   T N F G V R F R Y N A L G D L N T S N I V S S K E S F G I T
SACOL0129 (Strain COL)         T N F G V R F R Y N A L G D L N T S N I V S S K E S F G I T
SAB0085 (Strain RF122)         T N F G V R F R Y N A L G D L N T S N I V S S K E S F G I T
SAR0146 (Strain MRSA252)       T N F G V R F R Y N A L G D L N T S N I V S S K E S F G I T
SAV0144 (Strain Mu50)          T N F G V R F R Y N A L G D L N T S N I V S S K E S F G I T
SA0139 (Strain N315)           T N F G V R F R Y N A L G D L N T S N I V S S K E S F G I T
SAS0118 (Strain MSSA476)       T N F G V R F R Y N A L G D L N T S N I V S S K E S F G I T
MW0118 (Strain MW2)            T N F G V R F R Y N A L G D L N T S N I V S S K E S F G I T
                               T N F G V R F R Y N A L G D L N T S N I V S S K E S F G I T 220                 230                 240
SAUSA300_146 (Strain USA300)   E G V K S V S M H A G S T L A I T N P E K A K G I V Y T P E
SACOL0129 (Strain COL)         E G V K S V S M H A G S T L A I T N P E K A K G I V Y T P E
SAB0085 (Strain RF122)         E G V K S V S M H A G S T L A I T N P E K E K G I V Y T P E
SAR0146 (Strain MRSA252)       E G V K S V S M H A G S T L A I T N P E K A K G I V Y T P E
SAV0144 (Strain Mu50)          E G V K S V S M H A G S T L A I T N P E K A K G I V Y T P E
SA0139 (Strain N315)           E G V K S V S M H A G S T L A I T N P E K A K G I V Y T P E
SAS0118 (Strain MSSA476)       E G V K S V S M H A G S T L A I T N P E K A K G I V Y T P E
MW0118 (Strain MW2)            E G V K S V S M H A G S T L A I T N P E K A K G I V Y T P E
                               E G V K S V S M H A G S T L A I T N P E K A K G I V Y T P E 250                 260                 270
SAUSA300_146 (Strain USA300)   Q L P A K S K W S H A V D Q G I Y N G G G K A E G P Y V A I
SACOL0129 (Strain COL)         Q L P A K S K W S H A V D Q G I Y N G G G K A E G P Y V A I
SAB0085 (Strain RF122)         Q L P A K S K W S H A V D Q G I Y N G G G K A E G P Y V A I
SAR0146 (Strain MRSA252)       Q L P A K S K W S H A V D Q G I Y N G G G K A E G P Y V A I
SAV0144 (Strain Mu50)          Q L P A K S K W S H A V D Q G I Y N G G G K A E G P Y V A I
SA0139 (Strain N315)           Q L P A K S K W S H A V D Q G I Y N G G G K A E G P Y V A I
SAS0118 (Strain MSSA476)       Q L P A K S K W S H A V D Q G I Y N G G G K A E G P Y V A I
MW0118 (Strain MW2)            Q L P A K S K W S H A V D Q G I Y N G G G K A E G P Y V A I
                               Q L P A K S K W S H A V D Q G I Y N G G G K A E G P Y V A I 280                 290                 300
SAUSA300_146 (Strain USA300)   S K V G K G K A A F I G D S S L V E D S S P K Y V R E D N G
SACOL0129 (Strain COL)         S K V G K G K A A F I G D S S L V E D S S P K Y V R E D N G
SAB0085 (Strain RF122)         S K V G K G K A A F I G D S S L V E D S S P K Y V R E D N G
SAR0146 (Strain MRSA252)       S K V G K G K A A F I G D S S L V E D S S P K Y V R E D N G
SAV0144 (Strain Mu50)          S K V G K G K A A F I G D S S L V E D S S P K Y V R E D N G
SA0139 (Strain N315)           S K V G K G K A A F I G D S S L V E D S S P K Y V R E D N G
SAS0118 (Strain MSSA476)       S K V G K G K A A F I G D S S L V E D S S P K Y V R E D N G
MW0118 (Strain MW2)            S K V G K G K A A F I G D S S L V E D S S P K Y V R E D N G
                               S K V G K G K A A F I G D S S L V E D S S P K Y V R E D N G 310                 320                 330
SAUSA300_146 (Strain USA300)   E K K K T Y D G F K E Q D N G K L L N N I T A W M S K D N D
SACOL0129 (Strain COL)         E K K K T Y D G F K E Q D N G K L L N N I T A W M S K D N D
SAB0085 (Strain RF122)         E K K K T Y D G F K E Q D N G K L L N N I T A W M S K D N D
SAR0146 (Strain MRSA252)       E K K K T Y D G F K E Q D N G K L L N N I T A W M S K D N D
SAV0144 (Strain Mu50)          E K K K T Y D G F K E Q D N G K L L N N I T A W M S K D S D
SA0139 (Strain N315)           E K K K T Y D G F K E Q D N G K L L N N I T A W M S K D S D
SAS0118 (Strain MSSA476)       E K K K T Y D G F K E Q D N G K L L N N I T D W M S K D S D
MW0118 (Strain MW2)            E K K K T Y D G F K E Q D N G K L L N N I T D W M S K D S D
                               E K K K T Y D G F K E Q D N G K L L N N I T A W M S K D   D 340                 350                 360
SAUSA300_146 (Strain USA300)   G K S L K A S S L T L D T K T K L L D F E R P E R S T E P E
SACOL0129 (Strain COL)         G K S L K A S S L T L D T K T K L L D F E R P E R S T E P E
SAB0085 (Strain RF122)         G K S L K A S G L T L D T K T K L L D F E R P E R S T E P E
SAR0146 (Strain MRSA252)       G K S L K A S G L T L D T K T K L L D F E R P E R S T E P E
SAV0144 (Strain Mu50)          G K S L K A S G L T L D T K T K L L D F E R P E R S T E P E
SA0139 (Strain N315)           G K S L K A S G L T L D T K T K L L D F E R P E R S T E P E
SAS0118 (Strain MSSA476)       G K S L K A S G L T L D T K T K L L D F E R P E R S T E P E
MW0118 (Strain MW2)            G K S L K A S G L T L D T K T K L L D F E R P E R S T E P E
                               G K S L K A S G L T L D T K T K L L D F E R P E R S T E P E
```

FIG. 4B

|  | 370 | 380 | 390 |
|---|---|---|---|
| SAUSA300_146 (Strain USA300) | K E P W S Q P P S | G Y K W Y D P T T F | K A G S Y G S E K G A |
| SACOL0129 (Strain COL) | K E P W S Q P P S | G Y K W Y D P T T F | K A G S Y G S E K G A |
| SAB0085 (Strain RF122) | K E P W S Q P P S | G Y K W Y D P [K] T F | K A G S Y G S E K G A |
| SAR0146 (Strain MRSA252) | K E P W S Q P P S | G Y K W Y D P T T F | K A G S Y G S E K G A |
| SAV0144 (Strain Mu50) | K E P W S Q P P S | G Y K W Y D P T T F | K A G S Y G S E K G A |
| SA0139 (Strain N315) | K E P W S Q P P S | G Y K W Y D P T T F | K A G S Y G S E K G A |
| SAS0118 (Strain MSSA476) | K E P W S Q P P S | G Y K W Y D P T T F | K A G S Y G S E K G A |
| MW0118 (Strain MW2) | K E P W S Q P P S | G Y K W Y D P T T F | K A G S Y G S E K G A |
|  | K E P W S Q P P S | G Y K W Y D P T T F | K A G S Y G S E K G A |

|  | 400 | 410 | 420 |
|---|---|---|---|
| SAUSA300_146 (Strain USA300) | D P Q P N T P D D | H T P P N Q N E K V T F D | I P Q N V S V N |
| SACOL0129 (Strain COL) | D P Q P N T P D D | H T P P N Q N E K V T F D | I P Q N V S V N |
| SAB0085 (Strain RF122) | D P Q P N T P D D | H T P P N Q N E K V T F D | I P Q N V S V N |
| SAR0146 (Strain MRSA252) | D P Q P N T P D D | H T P P N Q N [V] K I S F D | I P Q N V S V N |
| SAV0144 (Strain Mu50) | D P Q P N T P D D | H T P P N Q N [T] E K V S F D | I P Q N V S V N |
| SA0139 (Strain N315) | D P Q P N T P D D | H T P P N Q N [V] K I S F D | I P Q N V S V N |
| SAS0118 (Strain MSSA476) | D P Q P N T P D D | H T P P N Q N E K V T F D | I P Q N V S V N |
| MW0118 (Strain MW2) | D P Q P N T P D D | H T P P N Q N E K V T F D | I P Q N V S V N |
|  | D P Q P N T P D D | H T P P N Q N E K V . F D | I P Q N V S V N |

|  | 430 | 440 | 450 |
|---|---|---|---|
| SAUSA300_146 (Strain USA300) | E P F E | M T I H L K G F E A N Q T L E N L R V G I Y K E G G |
| SACOL0129 (Strain COL) | E P F E | M T I H L K G F E A N Q T L E N L R V G I Y K E G G |
| SAB0085 (Strain RF122) | E P F E | V T I H L K G F E A N Q T L E N L R V G I Y K E G G |
| SAR0146 (Strain MRSA252) | E P F E | V T I H L K G F E A N Q T L E N L R V G I Y K E G G |
| SAV0144 (Strain Mu50) | E P F E | V T I H L K G F E A N Q T L E N L R V G I Y K E G G |
| SA0139 (Strain N315) | E P F E | V T I H L K G F E A N Q T L E N L R V G I Y K E G G |
| SAS0118 (Strain MSSA476) | E P F E | M T I H L K G F E A N Q T L E N L R V G I Y K E G G |
| MW0118 (Strain MW2) | E P F E | M T I H L K G F E A N Q T L E N L R V G I Y K E G G |
|  | E P F E | T I H L K G F E A N Q T L E N L R V G I Y K E G G |

|  | 460 | 470 | 480 |
|---|---|---|---|
| SAUSA300_146 (Strain USA300) | R Q I G Q F S S | K D N D Y N P P G Y S | T L P T V K A D E N G |
| SACOL0129 (Strain COL) | R Q I G Q F S S | K D N D Y N P P G Y S | T L P T V K A D E N G |
| SAB0085 (Strain RF122) | R Q I G Q F S S | K D N D Y N P P G Y S | T L P T V K A D E N G |
| SAR0146 (Strain MRSA252) | R Q I G Q F S S | K D N D Y N P P G Y S | T L P T V K A D E N G |
| SAV0144 (Strain Mu50) | R Q I G Q F S S | K D N D Y N P P G Y S | T L P T V K A D E N G |
| SA0139 (Strain N315) | R Q I G Q F S S | K D N D Y N P P G Y S | T L P T V K A D E N G |
| SAS0118 (Strain MSSA476) | R Q I G Q F S S | K D N D Y N P P G Y S | T L P T V K A D E N G |
| MW0118 (Strain MW2) | R Q I G Q F S S | K D N D Y N P P G Y S | T L P T V K A D E N G |
|  | R Q I G Q F S S | K D N D Y N P P G Y S | T L P T V K A D E N G |

|  | 490 | 500 | 510 |
|---|---|---|---|
| SAUSA300_146 (Strain USA300) | N V T I K V N A K V L E S | M E G S K I R L K L G D K T L I T |
| SACOL0129 (Strain COL) | N V T I K V N A K V L E S | M E G S K I R L K L G D K T L I T |
| SAB0085 (Strain RF122) | N A T I K V N A K V L E [R] | M E G S K I R L K L G D K T L I T |
| SAR0146 (Strain MRSA252) | N A T I K V N A K V L E S | M E G S K I R L K L G D K T L I T |
| SAV0144 (Strain Mu50) | N A T I K I N A K V L E S | M E G S K I R L K L G D K T L I T |
| SA0139 (Strain N315) | N A T I K I N A K V L E S | M E G S K I R L K L G D K T L I T |
| SAS0118 (Strain MSSA476) | N V T I K V N A K V L E S | M E G S K I R L K L G D K T L I T |
| MW0118 (Strain MW2) | N V T I K V N A K V L E S | M E G S K I R L K L G D K T L I T |
|  | N T I K V N A K V L E S | M E G S K I R L K L G D K T L I T |

|  | 520 |
|---|---|
| SAUSA300_146 (Strain USA300) | T D F K |
| SACOL0129 (Strain COL) | T D F K |
| SAB0085 (Strain RF122) | T D F K |
| SAR0146 (Strain MRSA252) | T D F K |
| SAV0144 (Strain Mu50) | T D F K |
| SA0139 (Strain N315) | T D F K |
| SAS0118 (Strain MSSA476) | T D F K |
| MW0118 (Strain MW2) | T D F K |
|  | T D F K |

FIG. 4C

ANTIBODIES RECOGNIZING A HIGHLY EXPRESSED PUTATIVE ANTIGEN OF CA-MRSA AND METHODS OF USE

CROSS REFERENCE TO RELATED APPLICATIONS

The present application claims the benefit of U.S. provisional application Ser. No. 60/775,356, filed Feb. 22, 2006, incorporated herein by reference.

FIELD OF THE INVENTION

The present invention relates to the fields of microbiology, molecular biology, and immunology and more particularly relates to newly identified MSCRAMM® proteins and polyclonal and monoclonal antibodies generated thereby, the use of such antibodies, as well as the production of such antibodies and recombinant host cells transformed with the DNA encoding monoclonal antibodies to prevent, treat, or diagnose *Staphylococcal aureus* infections in humans and animals. The invention includes murine, chimeric, humanized, and human monoclonal antibodies, as well as fragments, regions and derivatives thereof. The antibodies detailed in this invention specifically recognize a highly expressed putative antigen of CA-MRSA.

BACKGROUND OF THE INVENTION

*Staphylococcus aureus* is a resourceful pathogen that can cause disorders ranging from minor superficial infections to more serious and potentially fatal infections such as endocarditis and septicemia. In spite of antibiotic therapy, the mortality associated with these conditions has not diminished, presumably because methicillin resistant *S. aureus* (MRSA) is a major problem in hospitals. Alarmingly, MRSA has now emerged as a significant source of infections in communities worldwide, and the frequency of septicemia due to community acquired (CA) MRSA has been on the rise. In general, infections caused by *S. aureus* are generally difficult to treat, because these organisms are resistant to multiple antibiotics, and can form biofilms on the surface of the indwelling medical devices they infect.

Unfortunately, despite many attempts to prevent or treat the spread of this pathogen using antibiotic and non-antibiotic methods, there is still a need to develop new methods of controlling MRSA outbreaks and effectively treating those afflicted with MRSA infections and the pathogenic conditions caused thereby. It is therefore imperative that new strategies be developed which can address the critical problem of MRSA and particularly CA MRSA so as to stop or control outbreaks of this deadly pathogen in communities worldwide. In particular, it is highly desirable to develop treatments and compositions which can be useful in treating and preventing *Staphylococcus aureus* infections, particularly those caused by MRSA, and at the same time be useful in inhibiting the progression of staphylococcal infections in general.

SUMMARY OF THE INVENTION

It is thus an object of the present invention to provide compositions and methods for diagnosing, treating, and/or preventing infections caused by *Staphylococcus aureus*.

It is thus another object of the present invention to provide compositions and methods which are particularly useful in fighting MRSA infections such as CA-MRSA and which can inhibit the growth and severity of infections caused by MRSA and other staphylococcal bacteria.

It is still further an object of the present invention to isolate new MSCRAMM® proteins and polyclonal and monoclonal antibodies that recognize such proteins and to develop compositions that can be effective in identifying and isolating surface antigens from *Staphylococcus aureus* which can be useful in treating or preventing Staphylococcal diseases.

These and other objects are provided by the present invention wherein polyclonal and monoclonal antibody compositions recognizing the MW0118 protein from *S. aureus* can be administered to a patient in need of treatment for or protection against an infection caused by *Staphylococcus aureus*, and these compositions will be particularly effective in treating or preventing against infection from MRSA, such as community-associated MRSA. The MW0118 protein has been discovered to be a surface-associated MSCRAMM® protein from *S. aureus*, which means it is part of a group of related cell surface proteins from Gram-positive bacteria, collectively designated MSCRAMM® proteins (microbial surface components recognizing adhesive matrix molecules) which bind to major components of the ECM, such as collagens, fibronectin, laminin, fibrinogen, keratin, vitronectin and bone sialoprotein. MSCRAMM® proteins are mosaic proteins that typically consist of an N-terminal signal sequence for Sec-dependent transport across the cytoplasmic membrane, followed by an N-terminal A domain which exhibits the binding activity in most cases and repetitive B domains that confer fibronectin binding in a group of fibronectin binding MSCRAMM® protein. In the present case, MW0118 and its homologues from other *S. aureus* strains are capable of generating antibodies which can be effective in treating or preventing infections from *S. aureus*, particularly virulent infections such as from MRSA. Accordingly, in accordance with the present invention, these proteins may also be used in the form of vaccines in order to treat or prevent infection from CA-MRSA and other staphylococcal infections.

These and other objects of the present invention are obtained through the compositions and methods as set forth in the detailed description of the invention provided hereinbelow.

BRIEF DESCRIPTION OF THE DRAWING FIGURES

FIG. 1 illustrates A) A cell wall protein extraction; B) Western blot analysis using monoclonal anti-Spa IgG; and C) Western blot analysis using anti-SdrD polyclonal IgG wherein Lane 1 shows PVL-negative/φSLT-negative; Lane 2 shows PVL-negative/φSLT-positive; and Lane 3 shows PVL-positive/φSLT-positive.

FIG. 2 illustrates tests showing the fold decrease/increase levels of transcript from selected genes. Total RNA extracted from cultures grown at exponential (a) or stationary phase (b). Genes were considered to be induced or repressed in the PVL-positive strain if they were transcribed at least three fold higher/lower than in the PVL-negative strain. The shown transcripts encode: agr A-C, accessory regulator system; sarS, staphylococcal regulator S; spa, staphylococcal protein A; sdrD and C, serine aspartate proteins D and C; mw0118, putative cell-wall anchored protein; c/fB, clumping factor B; fnbpB, fibronectin binding protein B.

FIG. 3 is a schematic representation of protein MW0118 in accordance with the present invention. Sequence analysis and modeling programs predict a secretion signal (SS) and a non-repeated region (NRR) followed by a proline rich region.

At the N-terminus, MW0118 contains a putative sortase recognition sequence for anchoring to the cell wall (LPTV) and a highly charged transmembrane domain.

FIG. 4 comprises FIG. 4A-4C, which is a sequence alignment showing proteins in accordance with the present invention, along with a consensus sequence.

DETAILED DESCRIPTION OF THE PREFERRED EMBODIMENTS

In accordance with the present invention, novel MSCRAMM® proteins from S. aureus are provided which are putative highly-expressed antigens from methicillin-resistant S. aureus, including community-associated MRSA (CA-MRSA), and these antigens can thus be utilized in methods of generating antibodies capable of binding these antigens which can be useful in methods of treating or preventing infection from MRSA. The present invention thus is directed to these proteins, antibodies capable of binding these proteins, methods of generating said antibodies, nucleic acids coding for said proteins, and pharmaceutical compositions or vaccines which include the proteins or antibodies of the present invention in combination with a pharmaceutically acceptable vehicle, carrier or excipient.

As background to the present invention, most CA MRSA strains produce a toxin called Panton-Valentine Leukocidin and the presence of this toxin has been associated with enhanced binding to extracellular matrix components. Through experiments conducted in accordance with the invention, it has now been shown that PVL-positive CA-MRSA strains have an altered protein expression profile that results in the over-expression of cell surface adhesins giving these strains an advantage in their ability to invade and colonize the mammalian host. As the presence of the pvl locus appears to alter the expression profile of these bacterial strains, the global gene expression of PVL-negative (FIG. 1, lanes 1 and 2) and PVL-positive strains (FIG. 1, lane 3) was compared. To correlate the transcriptional profiles with our protein expression data (FIG. 1), we harvested total bacterial RNA from both strains at exponential and stationary phases. When compared to the PVL-negative strain, 88 genes show a different expression in the PVL-positive strain during logarithmic growth, whereas during the stationary phase, 673 genes show differential expression in the PVL-positive strain. A small group of differentially expressed genes, relevant to the focus of this proposal, is shown in FIG. 2. One of the most up-regulated genes in PVL-positive strains is a novel MSCRAMM® designated as MW0118 in the Staphylococcus aureus MW2 strain (which is homologous to SAS0118 in strain MSSA476, SACOL0129 in strain COL, SA0139 in strain N315, SAV0144 in strain Mu50, and SAR0146 in strain MRSA252, as shown in Table 1.0, below), and microarray analyses revealed the overexpression of MW0118 in a PVL+ strain.

We have now determined that MW0118 is a previously unidentified putative cell wall anchored protein with MSCRAMM® characteristics (FIG. 3) which is highly expressed in PVL+, CA MRSA strains. Additionally, we have determined that:

The expression of MW0118 may increase the virulence of CA MRSA strains;
Defined regions in MW0118 can be expressed as recombinant proteins to generate antibodies that block ligand binding;
Defined regions in MW0118 can therefore be used as vaccines;
Antibodies (polyclonal or monoclonal antibodies) can be generated against MW0118 that may interfere with the CA MRSA colonization and virulence; and
Antibodies (polyclonal or monoclonal antibodies) can be raised against MW0118 that be used as therapies against S. aureus infections.

Accordingly, the present invention is directed to the novel MSCRAMM® protein antigen designated as MW0118 in the Staphylococcus aureus MW2 strain, as well as to its homologues SAS0118 in strain MSSA476, SACOL0129 in strain COL, SA0139 in strain N315, SAV0144 in strain Mu50, and SAR0146 in strain MRSA252, all of which have been sequenced as set forth below. In addition, another aspect of the present invention is the provision of nucleic acids coding for these proteins, or nucleic acids that selectively hybridize to said sequences, as well as to monoclonal and polyclonal antibodies which recognize these proteins, and pharmaceutical compositions including the proteins or antibodies of the invention. Finally, the application is directed to methods of prevention and treatment of S. aureus infection using MW0118 or its homologues, nucleic acids coding for said proteins, or antibodies recognizing said proteins.

It is believed that the protein designated as MW0118 constitutes a novel virulence factor encoded by PVL+ CA MRSA. The increased expression of this protein had never been detected. The use of polyclonal or monoclonal antibodies reacting with MW0118 constitutes a new strategy for the prevention and treatment of infections caused by S. aureus. An analogous strategy, using antibodies targeted to the MSCRAMM® ClfA, has been effective in animal models for the treatment and prevention of infections caused by S. aureus. The MW0118 has been cloned, and can be expressed in E. coli, and protective monoclonal and polyclonal antibodies can be generated against it using the various conventional methods outlined below. MW0118 and its homologues have been isolated and sequenced, both with regard to protein and nucleic acid sequences, and this information is provided below.

In terms of methods of treating S. aureus, infections caused by S. aureus are generally difficult to treat, because these organisms are resistant to multiple antibiotics, and can form biofilms on the surface of the indwelling medical devices they infect. In accordance with the invention, MW0118 or its homologues may be used as an immunogen to constitute an excellent preparation to develop therapies to treat and prevent CA MRSA infections because the evidence shows that these proteins appear to be important and unique MRSA virulence factors. The advantage of using MW0118 and antibodies generated against the MW0118 as a treatment strategy for the prevention of S. aureus infections is that the humanized antibodies are very effective and do not cause secondary adverse reactions. This is a significant improvement over the antibiotic therapies that can be toxic to the host at high or prolonged doses and are ineffective in the necrotizing pneumonia cases.

The present invention thus outlines how to generate effective polyclonal and monoclonal antibodies for the prevention and treatment of infections caused by CA MRSA and related organisms. The populations of patients at risk are large and well defined: including healthy school-age children and young adults. An immunotherapeutic strategy is advantageous in these populations because the morbidity and mortality associated with hematogenously disseminated bacteremia and necrotizing pneumonia remains high, even with currently available antibiotic therapy. In addition, an increasing number of antibiotic-resistant strains is emerging, associated with the overuse of antibiotic agents, justifying the development of alternative and complementary therapeutic strategies.

In accordance with the present invention, peptides or recombinant proteins such as MW0118 or its homologues, or polypeptides that contain the active site(s) on MW0118 and thus are responsible for their extracellular matrix binding properties are included in the invention along with the use of these peptides or recombinant proteins as means of preventing S. aureus attachment to the host tissues.

As indicated above, antibodies in accordance with the present invention will be those antibodies capable of binding with the MW0118 protein or its homologues, and thus the present invention contemplates the generation of antibodies from these MSCRAMM® proteins obtained using methods of generating an immune response from these proteins or from antigenic regions from these proteins. By "antibody" is meant any intact antibody molecule or fragments thereof that recognize antigen (e.g. Fab or F(ab')2 fragments) and can be of polyclonal or monoclonal type, and the antibodies in accordance with the invention will be capable of recognizing the MSCRAMM® proteins of the invention and/or the specific antigenic epitopes from said proteins including their A domains or other immunogenic regions. These antibodies will thus be effective in methods of diagnosing, monitoring, treating or preventing infection from MRSA bacteria. By "epitope" is meant any antigenic determinant responsible for immunochemical binding with an antibody molecule. Epitopes usually reside within chemically active surface groupings of protein molecules (including amino acids and often also sugar side-chains) and have specific three-dimensional structural characteristics and specific charge characteristics. With reference to the proteins of the invention, or epitopes and peptides as described herein, it is understood that such terms also include those proteins and peptides which differ from a naturally occurring or recombinant protein by the substitution, deletion and/or addition of one or more amino acids but which retains the ability to be recognized by an antibody raised against the entire protein. An example is a carrier/antigen fusion polypeptide of the whole antigen or an immunoreactive fragment thereof, where the antigen or fragment can be embedded within the carrier polypeptide or linked to the carrier polypeptide at either end.

Accordingly, in accordance with the present invention, isolated and/or purified antibodies can be generated from the MSCRAMM® proteins of the present invention such as MW0118, or from particular epitopes such as those epitopic peptide sequences from the A domains from those proteins as described herein. These antibodies may be monoclonal or polyclonal and may be generated using any suitable method to raise such antibodies such as would be well known in this art. The antibodies in accordance with the invention will be particularly useful in inhibiting the binding of MRSA to extracellular matrix components of the host cells and in diagnosing, treating or preventing infections of MRSA bacteria.

For example, with regard to polyclonal antibodies, these may be generated using a number of suitable methods well known to the practitioner of ordinary skill in the art and these methods generally involve the injection of the isolated and/or purified or recombinantly produced proteins (or their immunogenic active peptides or epitopes) into a suitable host in order to generate the polyclonal antibodies which can then be recovered from the host. For example, in accordance with the invention, an isolated and purified MSCRAMM® protein or its A domain may be injected into rabbits in order to generate polyclonal antisera recognizing this protein.

In addition, monoclonal antibodies in accordance with the invention may be generated using a suitable hybridoma as would be readily understood by those of ordinary skill in the art. In the preferred process, a protein in accordance with the invention having a sequence as set forth below, which can thus be produced recombinantly using ordinary skill in the art, may be isolated and/or purified in any of a number of suitable ways commonly known in the art. In one suitable process, monoclonal antibodies may be generated from proteins isolated and purified as described above or by an addition of the protein with an adjuvant, and injecting the protein and/or mixture into BALB/c mice.

In general, the monoclonal antibodies of the invention may be produced using any of a variety of conventional methods, e.g., the method of Kohler and Milstein, Nature 256:495-497 (1975), or other suitable ways known in the field. In addition, it will be recognized that these monoclonals can be prepared in a number of forms, including chimeric, humanized, or human in addition to murine in ways that would be well known in this field. Still further, monoclonal antibodies may be prepared from a single chain, such as the light or heavy chains, and in addition may be prepared from active fragments of an antibody which retain the binding characteristics (e.g., specificity and/or affinity) of the whole antibody. By active fragments is meant an antibody fragment which has the same binding specificity as a complete antibody which binds to extracellular matrix binding proteins, and the term "antibody" as used herein is meant to include said fragments. Additionally, antisera prepared using monoclonal or polyclonal antibodies in accordance with the invention are also contemplated and may be prepared in a number of suitable ways as would be recognized by one skilled in the art.

In accordance with the invention, antibodies are thus produced which are capable of recognizing and binding to the putative highly expressed CA MRSA antigens as set forth above or epitopes and active regions from said proteins such as their A domain, and such antibodies can be utilized in many diagnostic and therapeutic applications such as the ones described in more detail below.

In another aspect of the present invention, the isolated antibodies of the present invention, or the isolated proteins or epitopes as described above, may also be utilized in the development of vaccines for active and passive immunization against bacterial infections, as described further below. In the case of active vaccines, said vaccines are prepared by providing an immunogenic amount of the proteins of the invention or their active regions or epitopes as set forth above, and the active vaccine in accordance with the invention will thus comprise an immunogenic amount of the protein or peptide and will be administered to a human or animal in need of such a vaccine. The vaccine may also comprise a suitable, pharmaceutically acceptable vehicle, excipient or carrier which will be those known and commonly used in the vaccine arts. As referred to above, an "immunogenic amount" of the antigen to be used in accordance with the invention is intended to mean a nontoxic but sufficient amount of the agent, such that an immunogenic response will be elicited in the host so that the desired prophylactic or therapeutic effect is produced. Accordingly, the exact amount of the antigen that is required will vary from subject to subject, depending on the species, age, and general condition of the subject, the severity of the condition being treated, the particular carrier or adjuvant being used and its mode of administration, and the like. Similarly, the "immunogenic amount" of any such antigenic vaccine composition will vary based on the particular circumstances, and an appropriate immunogenic amount may be determined in each case of application by one of ordinary skill in the art using only routine experimentation. The dose should be adjusted to suit the individual to whom the composition is administered and will vary with age, weight and metabolism of the individual.

Further, when administered as pharmaceutical composition to a patient or used to coat medical devices or polymeric biomaterials in vitro and in vivo, the antibodies of the present invention may also be useful because these antibodies may be able to interfere with the ability of MSRA bacteria to adhere to host cells and limit the extent and spread of the infection.

In addition, the antibody may be modified as necessary so that, in certain instances, it is less immunogenic in the patient to whom it is administered. For example, if the patient is a human, the antibody may be "humanized" by transplanting the complimentarily determining regions of the hybridoma-derived antibody into a human monoclonal antibody as described, e.g., by Jones et al., Nature 321:522-525 (1986) or Tempest et al. Biotechnology 9:266-273 (1991) or "veneered" by changing the surface exposed murine framework residues in the immunoglobulin variable regions to mimic a homologous human framework counterpart as described, e.g., by Padlan, Molecular 1 mm. 28:489-498 (1991), these references incorporated herein by reference. Even further, under certain circumstances, it may be desirable to combine the monoclonal antibodies of the present invention with a suitable antibiotic when administered so as to further enhance the ability of the present compositions to fight or prevent infections.

In a preferred embodiment, the antibodies may also be used as a passive vaccine which will be useful in providing suitable antibodies to treat or prevent a MSRA bacterial infection. As would be recognized by one skilled in this art, a vaccine may be packaged for administration in a number of suitable ways, such as by parenteral (i.e., intramuscular, intradermal or subcutaneous) administration or nasopharyngeal (i.e., intranasal) administration. One such mode is where the vaccine is injected intramuscularly, e.g., into the deltoid muscle, however, the particular mode of administration will depend on the nature of the bacterial infection to be dealt with and the condition of the patient. The vaccine is preferably combined with a pharmaceutically acceptable vehicle, carrier or excipient to facilitate administration, and the carrier is usually water or a buffered saline, with or without a preservative. The vaccine may be lyophilized for resuspension at the time of administration or in solution.

The preferred dose for administration of an antibody composition in accordance with the present invention is that amount will be effective in preventing of treating a bacterial infection, and one would readily recognize that this amount will vary greatly depending on the nature of the infection and the condition of a patient. An "effective amount" of antibody or pharmaceutical agent to be used in accordance with the invention is intended to mean a nontoxic but sufficient amount of the agent, such that the desired prophylactic or therapeutic effect is produced. Accordingly, the exact amount of the antibody or a particular agent that is required will vary from subject to subject, depending on the species, age, and general condition of the subject, the severity of the condition being treated, the particular carrier or adjuvant being used and its mode of administration, and the like. Accordingly, the "effective amount" of any particular antibody composition will vary based on the particular circumstances, and an appropriate effective amount may be determined in each case of application by one of ordinary skill in the art using only routine experimentation. The dose should be adjusted to suit the individual to whom the composition is administered and will vary with age, weight and metabolism of the individual.

The compositions may additionally contain stabilizers or pharmaceutically acceptable preservatives, such as thimerosal (ethyl(2-mercaptobenzoate-S)mercury sodium salt) (Sigma Chemical Company, St. Louis, Mo.).

In addition, the antibody compositions of the present invention and the vaccines as described above may also be administered with a suitable adjuvant in an amount effective to enhance the immunogenic response against the conjugate. For example, suitable adjuvants may include alum (aluminum phosphate or aluminum hydroxide), which is used widely in humans, and other adjuvants such as saponin and its purified component Quil A, Freund's complete adjuvant, and other adjuvants used in research and veterinary applications. Still other chemically defined preparations such as muramyl dipeptide, monophosphoryl lipid A, phospholipid conjugates such as those described by Goodman-Snitkoff et al. J. Immunol. 147:410-415 (1991) and incorporated by reference herein, encapsulation of the conjugate within a proteoliposome as described by Miller et al., J. Exp. Med. 176:1739-1744 (1992) and incorporated by reference herein, and encapsulation of the protein in lipid vesicles such as NOVASOME® lipid vesicles (Micro Vescular Systems, Inc., Nashua, N.H.) may also be useful.

Accordingly, the present invention provides polyclonal and monoclonal antibodies which recognize a highly expressed antigen from CA MRSA which can bind to S. aureus so as to be useful in methods of treating, preventing or diagnosing staphylococcal infections. The present invention thus contemplates these monoclonal antibodies, and other monoclonals recognizing the same epitopes of the specific monoclonals described herein. The present invention also contemplates proteins and antibodies which can be useful in methods of inhibiting adherence of S. aureus to host cells and thus treat or prevent a staphylococcal infection when used in amounts effective to prevent or treat such infections.

As would be recognized by one skilled in the art, the proteins and antibodies of the present invention may also be formed into suitable pharmaceutical compositions for administration to a human or animal patient in order to treat or prevent an infection caused by staphylococcal bacteria. Pharmaceutical compositions containing the proteins or antibodies of the present invention, or effective fragments thereof, e.g., antigen portions of the proteins, or effective portions of the antibodies such as fragments maintaining the binding properties of the whole antibody, may be formulated in combination with any suitable pharmaceutical vehicle, excipient or carrier that would commonly be used in this art, including such conventional materials for this purpose, e.g., saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill in this art. Suitable methods of administration, of any pharmaceutical composition disclosed in this application include, but are not limited to, topical, oral, anal, vaginal, intravenous, intraperitoneal, intramuscular, subcutaneous, intranasal and intradermal administration.

If topical administration is desired, the composition may be formulated as needed in a suitable form, e.g., an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

Additional forms of antibody or protein compositions are disclosed in other patents relating to MSCRAMM® proteins which will generally be applicable to the present invention as well, and these patents include U.S. Pat. Nos. 7,045,131; 6,994,855; 6,979,446; 6,841,154; 6,703,025; 6,692,739; 6,685,943; 6,680,195; 6,635,473; 6,288,214; 6,177,084; and 6,008,341, all of said patents incorporated herein by reference.

The antibody compositions of the present invention will thus be useful for interfering with, modulating, or inhibiting binding interactions of MRSA bacteria on host cells and tissues, and will thus have particular applicability in developing compositions and methods of preventing or treating staphylococcal infection, and in inhibiting binding of staphylococcal bacteria to host tissue and/or cells.

In accordance with the present invention, methods are provided for preventing or treating an MRSA infection which include administering an effective amount of the antibody of the present invention as described above in amounts effective to treat or prevent the infection. In addition, these antibodies will be useful in inhibiting *S. aureus* binding to the extracellular matrix of the host, and in reducing or eliminating the adherence of MRSA on host cells or on other surfaces, e.g., medical equipment, implants or prosthetics.

Accordingly, in accordance with the invention, administration of the antibodies of the present invention in any of the conventional ways described above (e.g., topical, parenteral, intramuscular, etc.), and will thus provide an extremely useful method of treating or preventing staphylococcal infections in human or animal patients. By effective amount is meant that level of use, such as of an antibody titer, that will be sufficient to either prevent adherence of the bacteria, to inhibit binding of *staph* bacteria to host cells and thus be useful in the treatment or prevention of a *staph* infection. As would be recognized by one of ordinary skill in this art, the level of antibody titer needed to be effective in treating or preventing staphylococcal infection will vary depending on the nature and condition of the patient, and/or the severity of the pre-existing staphylococcal infection.

In addition to the use of antibodies of the present invention to treat or prevent MRSA infections as described above, the present invention contemplates the use of these antibodies in a variety of ways, including the detection of the presence of MRSA to diagnose a *staph* infection, whether in a patient or on medical equipment, implants or prosthetics which may also become infected. In accordance with the invention, a preferred method of detecting the presence of *staph* infections involves the steps of obtaining a sample suspected of being infected by one or more staphylococcal bacteria species or strains, such as a sample taken from an individual, for example, from one's blood, saliva, tissues, bone, muscle, cartilage, or skin. The cells can then be lysed, and the DNA extracted, precipitated and amplified. Following isolation of the sample, diagnostic assays utilizing the antibodies of the present invention may be carried out to detect the presence of MRSA, and such assay techniques for determining such presence in a sample are well known to those skilled in the art and include methods such as radioimmunoassay, Western blot analysis and ELISA assays. In general, in accordance with the invention, a method of diagnosing an MRSA infection is contemplated wherein a sample suspected of being infected with MRSA infection has added to it the antibody in accordance with the present invention, and such an infection is indicated by antibody binding to the proteins in the sample.

Accordingly, antibodies in accordance with the invention may be used for the specific detection or diagnosis of staphylococcal proteins, for the prevention of infection from *staph* bacteria, for the treatment of an ongoing infection, or for use as research tools. The term "antibodies" as used herein includes monoclonal, polyclonal, chimeric, single chain, bispecific, simonized, and humanized or primatized antibodies as well as Fab fragments, such as those fragments which maintain the binding specificity of the antibodies to the MSCRAMM® proteins, including the products of an Fab immunoglobulin expression library.

When so desired for medical or research purposes, any of the above described antibodies may be labeled directly with a detectable label for identification and quantification of *staph* bacteria. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

Alternatively, the antibody may be labeled indirectly by reaction with labeled substances that have an affinity for immunoglobulin. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

Antibodies as described above may also be used in production facilities or laboratories to isolate additional quantities of the proteins, such as by affinity chromatography. For example, the antibodies of the invention may also be utilized to isolate additional amounts of the MSCRAMM® proteins or their active fragments.

The isolated antibodies of the present invention, or active fragments thereof, may also be utilized in the development of vaccines for passive immunization against *staph* infections. Further, when administered as pharmaceutical composition to a wound or used to coat medical devices or polymeric biomaterials in vitro and in vivo, the antibodies of the present invention, may be useful in those cases where there is a previous *staph* infection because of the ability of this antibody to further restrict and inhibit MRSA binding to host cells and thus limit the extent and spread of the infection. In addition, the antibody may be modified as necessary so that, in certain instances, it is less immunogenic in the patient to whom it is administered. For example, if the patient is a human, the antibody may be "humanized" by transplanting the complimentarily determining regions (CDR's) of the hybridoma-derived antibody into a human monoclonal antibody as described, e.g., by Jones et al., *Nature* 321:522-525 (1986) or Tempest et al. *Biotechnology* 9:266-273 (1991) or "veneered" by changing the surface exposed murine framework residues in the immunoglobulin variable regions to mimic a homologous human framework counterpart as described, e.g., by Padlan, *Molecular Imm.* 28:489-498 (1991) and U.S. Pat. No. 6,797,492, all of these references incorporated herein by reference. Even further, when so desired, the monoclonal antibodies of the present invention may be administered in conjunction with a suitable antibiotic to further enhance the ability of the present compositions to fight bacterial infections.

As indicated above, staphylococcal infections are not only a problem with patients but also may affect medical devices, implants and prosthetics, and thus the present invention can be utilized to protect these devices from staphylococcal infection as well, e.g., by coating these devices with the compositions of the present invention. Medical devices or polymeric biomaterials to be coated with the antibody compositions described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, other implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/uretheral/urinary devices (Foley catheters, stents, tubes and balloons), airway catheters (endrotracheal and tracheotomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the antibody or pharmaceutical composition derived therefrom, to a surface of the device, preferably an outer surface that would be exposed to streptococcal bacterial infection. The surface of the device need not be entirely covered by the protein, antibody or active fragment.

In a preferred embodiment, the antibodies may also be used as a passive vaccine which will be useful in providing suitable antibodies to treat or prevent a staphylococcal infection. As would be recognized by one skilled in this art, a vaccine may be packaged for administration in a number of suitable ways, such as by parenteral (i.e., intramuscular, intradermal or subcutaneous) administration or nasopharyngeal (i.e., intranasal) administration. One such mode is where the vaccine is injected intramuscularly, e.g., into the deltoid muscle, however, the particular mode of administration will depend on the nature of the bacterial infection to be dealt with and the condition of the patient. The vaccine is preferably combined with a pharmaceutically acceptable carrier to facilitate administration, and the carrier is usually water or a buffered saline, with or without a preservative. The vaccine may be lyophilized for resuspension at the time of administration or in solution.

The preferred dose for administration of an antibody composition in accordance with the present invention is that amount will be effective in preventing of treating a staphylococcal infection, and one would readily recognize that this amount will vary greatly depending on the nature of the infection and the condition of a patient. As indicated above, an "effective amount" of antibody or pharmaceutical agent to be used in accordance with the invention is intended to mean a nontoxic but sufficient amount of the agent, such that the desired prophylactic or therapeutic effect is produced. As will be pointed out below, the exact amount of the antibody or a particular agent that is required will vary from subject to subject, depending on the species, age, and general condition of the subject, the severity of the condition being treated, the particular carrier or adjuvant being used and its mode of administration, and the like. Accordingly, the "effective amount" of any particular antibody composition will vary based on the particular circumstances, and an appropriate effective amount may be determined in each case of application by one of ordinary skill in the art using only routine experimentation. The dose should be adjusted to suit the individual to whom the composition is administered and will vary with age, weight and metabolism of the individual. The compositions may additionally contain stabilizers or pharmaceutically acceptable preservatives, such as thimerosal (ethyl (2-mercaptobenzoate-S)mercury sodium salt) (Sigma Chemical Company, St. Louis, Mo.).

When used with suitable labels or other appropriate detectable biomolecule or chemicals, the monoclonal antibodies described herein are useful for purposes such as in vivo and in vitro diagnosis of staphylococcal infections or detection of staphylococcal bacteria. Laboratory research may also be facilitated through use of such antibodies. Various types of labels and methods of conjugating the labels to the antibodies of the invention are well known to those skilled in the art, such as the ones set forth below.

For example, the antibody can be conjugated (directly or via chelation) to a radiolabel such as, but not restricted to, $^{32}$P, $^{3}$H, $^{14}$C, $^{35}$S, $^{125}$I, or $^{131}$I. Detection of a label can be by methods such as scintillation counting, gamma ray spectrometry or autoradiography. Bioluminescent labels, such as derivatives of firefly luciferin, are also useful. The bioluminescent substance is covalently bound to the protein by conventional methods, and the labeled protein is detected when an enzyme, such as luciferase, catalyzes a reaction with ATP causing the bioluminescent molecule to emit photons of light. Fluorogens may also be used to label proteins. Examples of fluorogens include fluorescein and derivatives, phycoerythrin, allo-phycocyanin, phycocyanin, rhodamine, and TEXAS RED®. The fluorogens are generally detected by a fluorescence detector.

The location of a ligand in cells can be determined by labeling an antibody as described above and detecting the label in accordance with methods well known to those skilled in the art, such as immunofluorescence microscopy using procedures such as those described by Warren et al. (*Mol. Cell. Biol.*, 7: 1326-1337, 1987).

As indicated above, the antibodies of the present invention, or active portions or fragments thereof, are particularly useful for interfering with the initial physical interaction between a staphylococcal pathogen responsible for infection and a mammalian host, such as the adhesion of the bacteria to mammalian extracellular matrix proteins, and this interference with physical interaction may be useful both in treating patients and in preventing or reducing bacteria infection on in-dwelling medical devices to make them safer for use.

In another embodiment of the present invention, a kit which may be useful in isolating and identifying MRSA bacteria and infection is provided which comprises the antibodies of the present invention in a suitable form, such as lyophilized in a single vessel which then becomes active by addition of an aqueous sample suspected of containing the staphylococcal bacteria. Such a kit will typically include a suitable container for housing the antibodies in a suitable form along with a suitable immunodetection reagent which will allow identification of complexes binding to the antibodies of the invention. For example, the immunodetection reagent may comprise a suitable detectable signal or label, such as a biotin or enzyme that produces a detectable color, etc., which normally may be linked to the antibody or which can be utilized in other suitable ways so as to provide a detectable result when the antibody binds to the antigen.

As indicated above, the proteins and antibodies of the invention may also be formed into suitable pharmaceutical compositions for administration to a human or animal patient in order to treat or prevent an MRSA infection. Pharmaceutical compositions containing the proteins or antibodies of the present invention as defined and described above may be formulated in combination with any suitable pharmaceutical vehicle, excipient or carrier that would commonly be used in this art, including such as saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill in this art. Suitable methods of administration of any pharmaceutical composition disclosed in this application include, but are not limited to, topical, oral, anal, vaginal, intravenous, intraperitoneal, intramuscular, subcutaneous, intranasal and intradermal administration.

For topical administration, the composition may be formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

Additional forms of compositions, and other information concerning compositions, methods and applications with regard to other microbial surface proteins and peptides of the present invention and antibodies thereto, will be found in other patent references relating to MSCRAMM®s, including, for example, in U.S. Pat. No. 6,288,214 (Hook et al.), incorporated herein by reference.

In any event, the compositions of the present invention will thus be useful for interfering with, modulating, or inhibiting binding interactions by MRSA bacteria. Accordingly, the present invention will have particular applicability in developing compositions and methods of preventing or treating MRSA bacterial infections, and in inhibiting binding and spreading of bacteria to host cells.

In accordance with the present invention, the detection of MRSA bacteria present in a biological fluid (e.g. blood, serum, plasma, saliva, urine, cerebrospinal fluid, genitourinary tract) or other biological material (e.g., tissues, bone, muscle, cartilage, or skin) can constitute a method for the diagnosis of acute or chronic infections caused by MRSA. Because the antibodies as set forth above can recognize the epitopes found in MRSA, these antibodies can be used in assays to allow the diagnosis of an MRSA bacteria associated and disease conditions. Either monoclonal antibodies or polyclonal antibodies could be used in the assay, and in the case of the monoclonals such as those referred to above. The detected antigens identified by use of the present assays can be detected by a number of conventional means, including Western immunoblot and other similar tests.

With regard to the assays of the present invention, these assays may use the antibodies of the invention in labeled form, and all well-known methods of labeling antibodies are contemplated, including without limitation enzymatic conjugates, direct labeling with dye, radioisotopes, fluorescence, or particulate labels, such as liposome, latex, polystyrene, and colloid metals or nonmetals. Multiple antibody assay systems, such as antigen capture sandwich assays, are also within the scope of this invention. Further, competitive immunoassays involving labeled protein or assays using the labeled protein to detect serum antibodies are also contemplated forms of the diagnostic assays of the present invention. Beyond diagnostic assays which occur in solution, assays which involve immobilized antibody or protein are also considered within the scope of the invention. (See, for example, Miles et al., Lancet 2:492, 1968; Berry et al., J. Virol. Met. 34:91-100, 1991; Engvall et al., G. Immunochemistry, 8:871, 1971, Tom, Liposomes and Immunology, Elsevier/North Holland, New York, N.Y., 1980; Gribnau et al., J. of Chromatogr. 376:175-89, 1986 and all references cited therein). Examples of the types of labels which can be used in the present invention include, but are not limited to, enzymes, radioisotopes, fluorescent compounds, chemiluminescent compounds, bioluminescent compounds, particulates, and metal chelates. Those of ordinary skill in the art will know of other suitable labels for binding to the monoclonal or polyclonal antibody (or to an antigen) or will be able to ascertain the same by the use of routine experimentation. Furthermore, the binding of these labels to the monoclonal or polyclonal antibody (or antigen) can be accomplished using standard techniques commonly known to those of ordinary skill in the art.

One of the ways in which an assay reagent (generally, a monoclonal antibody, polyclonal antibody or antigen) of the present invention can be detectably labeled is by linking the monoclonal antibody, polyclonal antibody, or antigen to an enzyme. This enzyme, in turn, when later exposed to its substrate, will react with the substrate in such a manner as to produce a chemical moiety which can be detected as, for example, by spectrophotometric or fluorometric means. Examples of enzymes which can be used to detectably label the reagents of the present invention include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The presence of the detectably labeled reagent of the present invention can also be detected by labeling the reagent with a radioactive isotope which can then be determined by such means as the use of a gamma counter or a scintillation counter. Isotopes which are particularly useful for the purpose of the present invention are $^3H$, $^{125}I$, $^{32}P$, $^{35}S$, $^{14}C$, $^{51}Cr$, $^{36}Cl$, $^{57}Co$, $^{58}Co$, $^{59}Fe$ and $^{75}Se$. It is also possible to detect the binding of the detectably labeled reagent of the present invention by labeling the monoclonal or polyclonal antibody with a fluorescent compound. When the fluorescently labeled reagent is exposed to light of the proper wave length, its presence can then be detected due to the fluorescence of the dye. Among the most commonly used fluorescent labeling compounds are fluorescein isothiocyanate, rhodamine, phycoerythrin, phycocyanin, allophycocyanin, o-phthaldehyde and fluorescamine. The reagents of the present invention also can be detectably labeled by coupling it to a chemiluminescent compound. The presence of the chemiluminescent-tagged reagent is then determined by detecting the presence of luminescence that arises during the course of the chemical reaction. Examples of particularly useful chemiluminescent labeling compounds are luminol, isoluminol, theromatic acridinium ester, imidazole, acridinium salt and oxalate ester. Likewise, a bioluminescent compound may be used to label the reagent of the present invention. Bioluminescence is a type of chemiluminescence found in biological systems in which a catalytic protein increases the efficiency of the chemiluminescent reaction. The presence of a bioluminescent reagent is determined by detecting the presence of luminescence. Important bioluminescent compounds for purposes of labeling are luciferin, luciferase and aequorin.

Another technique which may also result in greater sensitivity when used in conjunction with the present invention consists of coupling the monoclonal or polyclonal antibody of the present invention to low molecular weight haptens. The haptens can then be specifically detected by means of a second reaction. For example, it is common to use such haptens as biotin (reacting with avidin) or dinitrophenol, pyridoxal and fluorescamine (reacting with specific antihapten antibodies) in this manner. Any biological sample containing the detectable yet unknown amount of an MRSA antigen can be used in the assay. Normally, the sample is preferably a liquid, such as, for example, urine, saliva, cerebrospinal fluid, blood, serum and the like, or a solid or semi-solid, such as, for example, tissue, feces and the like.

The diagnostic assay of the present invention includes kit forms of such an assay. This kit would include antibodies as described above (raised against whole proteins or active immunoreactive fragments such as the A domain or immunogenic analogs thereof) which can be optionally immobilized, as well as any necessary reagents and equipment to prepare the biological sample for and to conduct analysis, e.g. preservatives, reaction media such as nontoxic buffers, microtiter plates, micropipettes, etc. The reagent (Abs and/or antigens) can be lyophilized or cryopreserved. As described above, depending on the assay format, the antibodies can be labeled, or the kit can further comprise labeled proteins, fragments or analogs thereof containing the relevant epitopes so as to enable the detection of antibodies to MRSA proteins in biological fluids and tissues. By analog is meant a protein or peptide which may differs from its naturally occurring or recombinant counterpart by the substitution, deletion and/or addition of one or more amino acids but which retains the ability to be recognized by an antibody raised against the entire protein. An example is a carrier/antigen fusion polypeptide of the whole antigen or an immunoreactive fragment thereof, where the antigen or fragment can be embedded within the carrier polypeptide or linked to the carrier polypeptide at either end. Accordingly, antibodies in accordance with the invention may also recognize such analogs. The types of immunoassays which can be incorporated in kit form are many. Typical examples of some of the immunoassays which can utilize the antibodies of the invention are radioimmunoassays (RIA) and immunometric, or sandwich, immunoassays.

By "immunometric assay" or "sandwich immunoassay", in meant to include simultaneous sandwich, forward sandwich and reverse sandwich immunoassays. These terms are well understood by those skilled in the art. Those of skill will also appreciate that the monoclonal antibodies, polyclonal antibodies and/or antigens of the present invention will be useful in other variations and forms of immunoassays which are presently known or which may be developed in the future. These are intended to be included within the scope of the present invention. In a forward sandwich immunoassay, a sample is first incubated with a solid phase immunoabsorbent containing monoclonal or polyclonal antibody(ies) against the antigen. Incubation is continued for a period of time sufficient to allow the antigen in the sample to bind to the immobilized antibody in the solid phase. After the first incubation, the solid phase immunoabsorbent is separated from the incubation mixture and washed to remove excess antigen and other interfering substances, such as non-specific binding proteins, which also may be present in the sample. Solid phase immunoabsorbent containing antigen bound to the immobilized antibody is subsequently incubated for a second time with soluble labeled antibody or antibodies. After the second incubation, another wash is performed to remove unbound labeled antibody(ies) from the solid phase immunoabsorbent and removing non-specifically bound labeled antibody(ies). Labeled antibody(ies) bound to the solid phase immunoabsorbent is then detected and the amount of labeled antibody detected serves as a direct measure of the amount of antigen present in the original sample.

Alternatively, labeled antibody which is not associated with the immunoabsorbent complex can also be detected, in which case the measure is in inverse proportion to the amount of antigen present in the sample. Forward sandwich assays are described, for example, in U.S. Pat. Nos. 3,867,517; 4,012,294 and 4,376,110, incorporated herein by reference. In carrying out forward immunometric assays, the process may comprise, in more detail: (a) first forming a mixture of the sample with the solid phase bound antibody(ies) and incubating the mixture for a time and under conditions sufficient to allow antigen in the sample to bind to the solid phase bound antibody(ies), (b) adding to the mixture after said incubation of step (a) the detectably labeled antibody or antibodies and incubating the new resulting mixture for a time and under conditions sufficient to allow the labeled antibody to bind to the antigen-antibody complex on the solid phase immunoabsorbent; (c) separating the solid phase immunoabsorbent from the mixture after the incubation in step (b); and (d) detecting either the labeled antibody or antibodies bound to the antigen-antibody complex on the solid phase immunoabsorbent or detecting the antibody not associated therewith.

In a reverse sandwich assay, the sample is initially incubated with labeled antibody(ies), after which the solid phase immunoabsorbent containing multiple immobilized antibodies is added thereto, and a second incubation is carried out. The initial washing step of a forward sandwich assay is not required, although a wash is performed after the second incubation. Reverse sandwich assays have been described, for example, in U.S. Pat. Nos. 4,098,876 and 4,376,110. In carrying out reverse immunometric assays, the process may comprise, in more detail; (a) first forming a mixture of the sample with the soluble detectably labeled antibody for a time and under conditions sufficient to allow antigen in the sample to bind to the labeled antibody; (b) adding to the mixture after the incubation of step (a) the solid phase bound antibodies and incubating the new resulting mixture for a time and under conditions sufficient to allow antigen bound to the labeled antibody to bind to the solid phase antibodies; (c) separating the solid phase immunoabsorbent from the incubating mixture after the incubation in step (b); and (d) detecting either the labeled antibody bound to the solid phase immunoabsorbent or detecting the labeled antibody not associated therewith.

In yet another aspect of the invention, nucleic acids are provided which encode the MSCRAMM® proteins of the present invention. Such nucleic acids include those degenerate sequences which encode the same proteins, as well as those nucleic acids which can selectively hybridize with the nucleic acids coding for the MSCFRAMM® proteins of the invention.

As indicated above, the present invention relates to putative highly expressed antigens from CA MRSA which have been isolated and sequenced, and which can be used to generate antibodies capable of treating or preventing MRSA invention. These protein sequences and the nucleic acid sequences coding for them are set forth below.

The following are the sequences of the proteins of the present invention followed by an alignment of the protein from several genomic databases.

MW0118 (Strain MW2)
(SEQ ID NO: 1)
MKKIYKSLTVSAIVATVSLSALPQSLAITHESQPTKQQRTVLFDRSHGQT

AGAADWVSDGAFSDYADSIQKQGYDVKAIDGHSNITEASLKSSKIFVIPE

ANIPFKESEQAAIVNYVKQGGNVVFISDHYNADRNLNRIDSSEAMNGYRR

GAYEDMSKGMNAEEKSSTAMQGVKSSDWLSTNFGVRFRYNALGDLNTSNI

VSSKESFGITEGVKSVSMHAGSTLAITNPEKAKGIVYTPEQLPAKSKWSH

AVDQGIYNGGGKAEGPYVAISKVGKGAAFIGDSSLVEDSSPKYVREDNGE

KKKTYDGFKEQDNGKLLNNITDWMSKDSDGKSLKASGLTLDTKTKLLDFE

RPERSTEPEKEPWSQPPSGYKWYDPTTFKAGSYGSEKGADPQPNTPDDHT

PPNQNEKVTFDIPQNVSVNEPFEMTIHLKGFEANQTLENLRVGIYKEGGR

QIGQFSSKDNDYNPPGYSTLPTVKADENGNVTIKVNAKVLESMEGSKIRL

KLGDKTLITTDFK

MW0118 (Strain MW2) Nucleic acid sequence
(SEQ ID NO: 2)
ATGAAAAAAATATATAAGTCATTAACTGTCTCTGCAATTGTTGCAACGGT

ATCATTAAGTGCTTTACCGCAATCTTTAGCTATAACGCATGAATCGCAAC

CTACAAAGCAACAGCGAACGGTATTATTCGATCGTTCTCATGGTCAAACA

GCTGGTGCTGCAGATTGGGTTAGTGATGGTGCATTTTCAGATTATGCGGA

TTCAATACAAAAACAAGGTTATGACGTTAAAGCTATTGATGGTCATTCGA

ACATAACAGAAGCAAGTTTGAAAAGTTCTAAAATATTTGTAATTCCTGAG

GCTAATATTCCTTTCAAAGAATCAGAACAGGCAGCAATTGTTAACTATGT

GAAACAAGGTGGCAATGTTGTCTTTATTTCAGATCATTACAATGCTGACC

GAAATTTAAATCGTATTGATTCATCAGAGGCAATGAATGGTTATCGACGT

GGAGCATATGAAGATATGTCGAAAGGTATGAATGCAGAAGAAAAAAGTTC

TACTGCAATGCAAGGTGTGAAAAGTTCAGATTGGTTATCTACAAACTTTG

GCGTACGTTTTCGATATAATGCACTAGGTGATTTAAATACGAGCAATATT

GTTTCTTCAAAAGAGTTTCGGTATTACTGAAGGTGTGAAATCTGTCTC

TATGCATGCCGGATCAACATTAGCAATTACTAATCCAGAGAAAGCAAAG

GTATTGTGTATACACCAGAACAATTGCCAGCGAAAAGTAAATGGTCACAT

GCTGTAGATCAAGGTATTTATAATGGGGGCGGTAAAGCAGAAGGCCCCTA

TGTAGCAATTTCTAAAGTTGGAAAAGGTAAAGCAGCATTTATCGGTGATT

CATCACTTGTGGAAGATAGTTCGCCCAAATATGTAAGAGAAGATAATGGA

GAAAAGAAGAAAACATATGATGGTTTTAAAGAACAAGACAACGGTAAGCT

ATTAAATAATATAACGGATTGGATGTCTAAAGATAGTGATGGGAAATCAC

TTAAGGCGAGTGGACTAACATTAGATACAAAGACTAAGTTGCTTGATTTT

GAACGACCAGAGCGTTCAACTGAGCCTGAAAAAGAGCCATGGTCACAACC

GCCGAGTGGTTATAAATGGTATGATCCAACAACATTTAAAGCAGGTAGTT

ATGGCAGCGAAAAAGGCGCAGATCCTCAGCCAAACACACCAGATGATCAT

ACGCCACCAAATCAGAACGAAAAAGTAACATTTGATATCCCGCAAAATGT

TTCTGTAAATGAGCCATTTGAAATGACAATACATTTAAAAGGATTTGAAG

CAAATCAAACACTTGAAAATCTTAGAGTTGGTATTTACAAAGAAGGCGGA

CGTCAAATCGGACAATTTTCAAGTAAAGATAACGATTATAACCCACCAGG

TTACAGTACTTTGCCAACAGTTAAAGCAGATGAAAACGGAAATGTCACAA

TTAAGGTCAATGCTAAAGTACTTGAAAGTATGGAAGGTTCAAAGATTCGT

TTAAAACTCGGTGACAAAACCTTGATTACAACAGACTTCAAATAA

SAS0118 (Strain MSSA476)
(SEQ ID NO: 3)
MKKIYKSLTVSAIVATVSLSALPQSLAITHESQPTKQQRTVLFDRSHGQT

AGAADWVSDGAFSDYADSIQKQGYDVKAIDGHSNITEASLKSSKIFVIPE

ANIPFKESEQAAIVNYVKQGGNVVFISDHYNADRNLNRIDSSEAMNGYRR

GAYEDMSKGMNAEEKSSTAMQGVKSSDWLSTNFGVRFRYNALGDLNTSNI

VSSKESFGITEGVKSVSMHAGSTLAITNPEKAKGIVYTPEQLPAKSKWSH

AVDQGIYNGGGKAEGPYVAISKVGKGAAFIGDSSLVEDSSPKYVREDNG

EKKKTYDGFKEQDNGKLLNNITDWMSKDSDGKSLKASGLTLDTKTKLLDF

ERPERSTEPEKEPWSQPPSGYKWYDPTTFKAGSYGSEKGADPQPNTPDDH

TPPNQNEKVTDIPQNVSVNEPFEMTIHLKGFEANQTLENLRVGIYKEGGR

QIGQFSSKDNDYNPPGYSTLPTVKADENGNVTIKVNAKVLESMEGSKIRL

KLGDKTLITTDFK

SAS0118 (Strain MSSA476) Nucreic acid sequence
(SEQ ID NO: 4)
ATGAAAAAAATATATAAGTCATTAACTGTCTCTGCAATTGTTGCAACGGT

ATCATTAAGTGCTTTACCGCAATCTTTAGCTATAACGCATGAATCGCAAC

CTACAAAGCAACAGCGAACGGTATTATTCGATCGTTCTCATGGTCAAACA

GCTGGTGCTGCAGATTGGGTTAGTGATGGTGCATTTTCAGATTATGCGGA

TTCAATACAAAAACAAGGTTATGACGTTAAAGCTATTGATGGTCATTCGA

ACATAACAGAAGCAAGTTTGAAAAGTTCTAAAATATTTGTAATTCCTGAG

GCTAATATTCCTTTCAAAGAATCAGAACAGGCAGCAATTGTTAACTATGT

GAAACAAGGTGGCAATGTTGTCTTTATTTCAGATCATTACAATGCTGACC

GAAATTTAAATCGTATTGATTCATCAGAGGCAATGAATGGTTATCGACGT

GGAGCATATGAAGATATGTCGAAAGGTATGAATGCAGAAGAAAAAAGTTC

TACTGCAATGCAAGGTGTGAAAAGTTCAGATTGGTTATCTACAAACTTTG

GCGTACGTTTTCGATATAATGCACTAGGTGATTTAAATACGAGCAATATT

GTTTCTTCAAAAGAGTTTCGGTATTACTGAAGGTGTGAAATCTGTCTC

TATGCATGCCGGATCAACATTAGCAATTACTAATCCAGAGAAAGCAAAG

GTATTGTGTATACACCAGAACAATTGCCAGCGAAAAGTAAATGGTCACAT

GCTGTAGATCAAGGTATTTATAATGGGGGCGGTAAAGCAGAAGGCCCCTA

TGTAGCAATTTCTAAAGTTGGAAAAGGTAAAGCAGCATTTATCGGTGATT
CATCACTTGTGGAAGATAGTTCGCCCAAATATGTAAGAGAAGATAATGGA
GAAAAGAAGAAAACATATGATGGTTTTAAAGAACAAGACAACGGTAAGCT
ATTAAATAATATAACGGATTGGATGTCTAAAGATAGTGATGGGAAATCAC
TTAAGGCGAGTGGACTAACATTAGATACAAAGACTAAGTTGCTTGATTTT
GAACGACCAGAGCGTTCAACTGAGCCTGAAAAGAGCCATGGTCACAACC
GCCGAGTGGTTATAAATGGTATGATCCAACAACATTTAAAGCAGGTAGTT
ATGGCAGCGAAAAGGCGCAGATCCTCAGCCAAACACACCAGATGATCAT
ACGCCACCAAATCAGAACGAAAAGTAACATTTGATATCCCGCAAAATGT
TTCTGTAAATGAGCCATTTGAAATGACAATACATTTAAAAGGATTTGAAG
CAAATCAAACACTTGAAAATCTTAGAGTTGGTATTTACAAAGAAGGCGGA
CGTCAAATCGGACAATTTTCAAGTAAAGATAACGATTATAACCCACCAGG
TTACAGTACTTTGCCAACAGTTAAAGCAGATGAAAACGGAAATGTCACAA
TTAAGGTCAATGCTAAAGTACTTGAAAGTATGGAAGGTTCAAAGATTCGT
TTAAAACTCGGTGACAAAACCTTGATTACAACAGACTTCAAATAA

SA0139 (Strain N315)
(SEQ ID NO: 5)
MKKIYKSLTVSAIVATVSLSALPQSLAITHESQPTKQQRTVLFDRSHGQT
AGAADWVSDGAFSDYADSIQKQGYDVKAIDGHSNITEASLKSSKIFVIPE
ANIPFKESEQAAIVNYVKQGGNVVFISDHYNADRNLNRIDSSEAMNGYRR
GAYEDMSKGMNAEEKSSTAMQGVKSSDWLSTNFGVRFRYNALGDLNTSNI
VSSKESFGITEGVKSVSMHAGSTLAITNPEKAKGIVYTPEQLPAKSKWSH
AVDQGIYNGGGKAEGPYVAISKVGKGKAAFIGDSSLVEDSSPKYVREDNG
EKKKTYDGFKEQDNGKLLNNITAWMSKDSDGKSLKASGLTLDTKTKLLDF
ERPERSTEPEKEPWSQPPSGYKWYDPTTFKAGSYGSEKGADPQPNTPDDH
TPPNQNVKISFDIPQNVSVNEPFEVTIHLKGFEANQTLENLRVGIYKEGG
RQIGQFSSKDNDYNPPGYSTLPTVKADENGNATIKINAKVLESMEGSKIR
LKLGDKTLITTDFK SA0139 (Strain N315) Nucleic acid sequence
(SEQ ID NO: 6)
ATGAAAAAAATATATAAGTCATTAACTGTCTCTGCAATTGTTGCAACGGT
ATCATTAAGTGCTTTACCGCAATCTTTAGCTATAACGCATGAATCGCAAC
CTACAAAGCAACAGCGAACGGTATTATTCGATCGTTCTCATGGTCAAACA
GCTGGTGCTGCAGATTGGGTTAGTGATGGTGCATTTTCAGATTATGCGGA
TTCAATACAAAAACAAGGTTATGACGTTAAAGCTATTGATGGTCATTCGA
ACATAACAGAAGCAAGTTTGAAAAGTTCCAAAATATTTGTAATTCCTGAG
GCTAACATTCCTTTCAAAGAATCAGAACAGGCAGCAATTGTTAACTATGT
GAAACAAGGTGGCAATGTTGTCTTTATTTCAGATCATTACAATGCTGACC
GAAATTTAAATCGTATTGATTCATCGGAGGCAATGAATGGTTATCGACGT
GGAGCATATGAAGATATGTCGAAAGGTATGAATGCAGAAGAAAAAGCTC
TACTGCAATGCAAGGTGTGAAAAGTTCAGATTGGTTATCTACAAACTTTG
GCGTACGTTTTCGATATAATGCACTAGGTGATTTAAATACGAGCAATATT GTTTCTTCAAAAGAAAGTTTCGGTATTACTGAAGGTGTGAAATCTGTCTC
TATGCATGCCGGATCGACATTAGCAATTACTAATCCAGAGAAAGCAAAAG
GTATTGTGTATACACCAGAACAATTGCCAGCGAAAAGTAAATGGTCACAT
GCTGTAGATCAAGGTATTTATAATGGTGGCGGTAAAGCAGAAGGCCCCTA
TGTAGCAATTTCTAAAGTTGGAAAAGGTAAAGCAGCATTTATCGGTGATT
CATCACTTGTGGAAGATAGTTCGCCCAAATATGTAAGAGAAGATAATGGA
GAAAAGAAGAAAACATATGATGGTTTTAAAGAACAAGACAACGGTAAGCT
ATTAAATAATATAACGGCTTGGATGTCTAAAGATAGTGATGGGAAATCAC
TTAAGGCGAGTGGACTAACATTAGATACAAAGACTAAGTTGCTTGATTTT
GAACGACCAGAGCGTTCAACTGAGCCTGAAAAGAGCCATGGTCACAACC
GCCGAGTGGTTATAAATGGTATGACCCAACAACATTTAAAGCAGGTAGTT
ATGGCAGTGAAAAGGCGCGGATCCTCAGCCAAACACACCAGATGATCAT
ACGCCACCAAATCAGAACGTAAAAATATCATTTGATATCCCGCAAAATGT
TTCTGTAAATGAGCCATTTGAAGTGACAATACATTTAAAAGGATTTGAAG
CAAATCAAACACTTGAAAATCTTAGAGTTGGTATTTACAAAGAAGGCGGA
CGTCAAATCGGACAATTTTCAAGTAAAGATAACGATTATAACCCACCAGG
TTACAGTACTTTGCCAACAGTTAAAGCAGATGAAAACGGAAATGCTACAA
TTAAGATCAATGCTAAAGTACTTGAAAGTATGGAAGGTTCAAAGATTCGT
TTAAAACTCGGTGACAAAACCTTGATTACAACAGACTTCAAATAA SACOL0129 (Strain COL)
(SEQ ID NO: 7)
MKKIYKSLTVSAIVATVSLSALPQSLAITHESQPTKQQRTVLFDRSHGQT
AGAADWVSDGAFSDYADSIQKQGYDVKAIDGHSNITEASLKSSKIFVIPE
ANIPFKESEQAAIVKYVKQGGNVVFISDHYNADRNLNRIDSSEAMNGYRR
GAYEDMSKGMNAEEKSSTAMQGVKSSDWLSTNFGVRFRYNALGDLNTSNI
VSSKESFGITEGVKSVSMHAGSTLAITNPEKAKGIVYTPEQLPAKSKWSH
AVDQGIYNGGGKAEGPYVAISKVGKGKAAFIGDSSLVEDSSPKYVREDNG
EKKKTYDGFKEQDNGKLLNNITAWMSKDNDGKSLKASSLTLDTKTKLLDF
ERPERSTEPEKEPWSQPPSGYKWYDPTTFKAGSYGSEKGADPQPNTPDDH
TPPNQNEKVTFDIPQNVSVNEPFEMTIHLKGFEANQTLENLRVGIYKEGG
RQIGQFSSKDNDYNPPGYSTLPTVKADENGNVTIKVNAKVLESMEGSKIR
LKLGDKTLITTDFK SACOL0129 (Strain COL) Nucleic acid sequence
(SEQ ID NO: 8)
ATGAAAAAAATATATAAGTCATTAACTGTCTCTGCAATTGTTGCAACGGT
ATCATTAAGTGCTTTACCGCAATCTTTAGCTATAACGCATGAATCGCAAC
CTACAAAGCAACAGCGAACGGTATTATTCGATCGTTCTCATGGTCAAACA
GCTGGTGCTGCAGATTGGGTTAGTGATGGTGCATTTTCAGATTATGCGGA
TTCAATACAAAAACAAGGTTATGACGTTAAAGCTATTGATGGTCATTCGA
ACATAACGAAGCAAGTTTGAAAAGTTCCAAAATATTTGTAATTCCTGAG
GCTAACATTCCTTTCAAAGAATCAGAACAGGCAGCAATTGTTAAATATGT
GAAACAAGGTGGCAATGTTGTCTTTATTTCAGATCATTACAATGCTGACC -continued

```
GAAATTTAAATCGTATTGATTCATCGGAGGCAATGAATGGTTATCGACGT

GGAGCATATGAAGATATGTCGAAAGGTATGAATGGAGAAGAAAAAGTTC

TACTGCAATGCAAGGTGTGAAAAGTTCAGATTGGTTATCTACAAACTTTG

GCGTACGTTTTCGATATAATGCACTAGGTGATTTAAATACGAGCAATATT

GTTTCTTCAAAAGAAAGTTTCGGTATTACTGAAGGTGTGAAATCTGTCTC

TATGCATGCCGGATCGACATTAGCAATTACTAATCCAGAGAAAGCAAAAG

GTATTGTGTATACACCAGAACAATTGCCAGCGAAAAGTAAATGGTCACAT

GCTGTAGATCAAGGTATTTATAATGGGGGCGGTAAAGCAGAAGGCCCCTA

TGTAGCAATTTCTAAAGTTGGAAAAGGTAAAGCAGCATTTATCGGTGATT

CATCACTTGTGGAAGATAGTTCGCCCAAATATGTAAGAGAAGATAATGGA

GAAAAGAAGAAAACATATGATGGTTTTAAAGAACAAGACAACGGTAAGCT

ATTAAATAATATAACGGCTTGGATGTCTAAAGATAATGATGGGAAATCAC

TTAAGGCGAGTAGCCTAACATTAGATACAAAGACTAAGTTGCTTGATTTT

GAACGACCAGAGCGTTCAACTGAGCCTGAAAAGAGCCATGGTCACAACC

GCCGAGTGGTTATAAATGGTATGATCCAACAACATTTAAAGCAGGTAGTT

ATGGCAGCGAAAAGGCGCAGATCCTCAGCCAAACACACCAGATGATCAT

ACACCACCAAATCAGAACGAAAAAGTAACATTTGATATCCCGCAAAATGT

TTCTGTAAATGAGCCATTTGAAATGACAATACATTTAAAAGGATTTGAAG

CAAATCAAACACTTGAAAATCTTAGAGTTGGTATTTACAAAGAAGGCGGA

CGTCAAATCGGACAATTTTCAAGTAAAGATAACGATTATAACCCACCAGG

TTACAGTACTTTGCCAACAGTTAAAGCAGATGAAAACGGAAATGTCACAA

TTAAGGTCAATGCTAAAGTACTTGAAAGTATGGAAGGTTCAAAGATTCGT

TTAAAAACTCGGTGACAAAACCTTGATTACAACAGACTTCAAATAA
```

SAV0144 (Strain Mu50)

(SEQ ID NO: 9)

```
MKKIYKSLTVSAIVATVSLSALPQSLAITHESQPTKQQRTVLFDRSHGQT
AGAADWVSDGAFSDYADSIQKQGYDVKAIDGHSNITEASLKSSKIFVIPE
ANIPFKESEQAAIVNYVKQGGNVVFISDHYNADRNLNRIDSSEAMNGYRR
GAYEDMSKGMNAEEKSSTAMQGVKSSDWLSTNFGVRFRYNALGDLNTSNI
VSSKESFGITEGVKSVSMHAGSTLAITNPEKAKGIVYTPEQLPAKSKWSH
AVDQGIYNGGGKAEGPYVAISKVGKGKAAFIGDSSLVEDSSPKYVREDNG
EKKKTYDGFKEQDNGKLLNNITAWMSKDSDGKSLKASGLTLDTKTKLLDF
ERPERSTEPEKEPWSQPPSGYKWYDPTTFKAGSYGSEKGADPQPNTPDDH
TPPNQNVKISFDIPQNVSVNEPFEVTIHLKGFEANQTLENLRVGIYKEGG
RQIGQFSSKDNDYNPPGYSTLPTVKADENGNATIKINAKVLESMEGSKIR
LKLGDKTLITTDFK
```

SAV0144 (Strain Mu50) Nucleic acid sequence (SEQ ID NO: 10)

```
ATGAAAAAAATATATAAGTCATTAACTGTCTCTGCAATTGTTGCAACGGT
ATCATTAAGTGCTTTACCGCAATCTTTAGCTATAACGCATGAATCGCAAC
CTACAAAGCAACAGCGAACGGTATTATTCGATCGTTCTCATGGTCAAACA
GCTGGTGCTGCAGATTGGGTTAGTGATGGTGCATTTTCAGATTATGCGGA
```

```
TTCAATACAAAAACAAGGTTATGACGTTAAAGCTATTGATGGTCATTCGA

ACATAACGAAGCAAGTTTGAAAAGTTCCAAATATTTGTAATTCCTGAG

GCTAACATTCCTTTCAAAGAATCAGAACAGGCAGCAATTGTTAACTATGT

GAAACAAGGTGGCAATGTTGTCTTTATTTCAGATCATTACAATGCTGACC

GAAATTTAAATCGTATTGATTCATCGGAGGCAATGAATGGTTATCGACGT

GGAGCATATGAAGATATGTCGAAAGGTATGAATGCAGAAGAAAAAGCTC

TACTGCAATGCAAGGTGTGAAAAGTTCAGATTGGTTATCTACAAACTTTG

GCGTACGTTTTCGATATAATGCACTAGGTGATTTAAATACGAGCAATATT

GTTTCTTCAAAAGAAAGTTTCGGTATTACTGAAGGTGTGAAATCTGTCTC

TATGCATGCCGGATCGACATTAGCAATTACTAATCCAGAGAAAGCAAAAG

GTATTGTGTATACACCAGAACAATTGCCAGCGAAAAGTAAATGGTCACAT

GCTGTAGATCAAGGTATTTATAATGGTGGCGGTAAAGCAGAAGGCCCCTA

TGTAGCAATTTCTAAAGTTGGAAAAGGTAAAGCAGCATTTATCGGTGATT

CATCACTTGTGGAAGATAGTTCGCCCAAATATGTAAGAGAAGATAATGGA

GAAAAGAAGAAAACATATGATGGTTTTAAAGAACAAGACAACGGTAAGCT

ATTAAATAATATAACGGCTTGGATGTCTAAAGATAGTGATGGGAAATCAC

TTAAGGCGAGTGGACTAACATTAGATACAAAGACTAAGTTGCTTGATTTT

GAACGACCAGAGCGTTCAACTGAGCCTGAAAAGAGCCATGGTCACAACC

GCCGAGTGGTTATAAATGGTATGACCCAACAACATTTAAAGCAGGTAGTT

ATGGCAGTGAAAAGGCGCGGATCCTCAGCCAAACACACCAGATGATCAT

ACGCCACCAAATCAGAACGTAAAAATATCATTTGATATCCCGCAAAATGT

TTCTGTAAATGAGCCATTTGAAGTGACAATACATTTAAAAGGATTTGAAG

CAAATCAAACACTTGAAAATCTTAGAGTTGGTATTTACAAAGAAGGCGGA

CGTCAAATCGGACAATTTTCAAGTAAAGATAACGATTATAACCCACCAGG

TTACAGTACTTTGCCAACAGTTAAAGCAGATGAAAACGGAAATGCTACAA

TTAAGATCAATGCTAAAGTACTTGAAAGTATGGAAGGTTCAAAGATTCGT

TTAAAAACTCGGTGACAAAACCTTGATTACAACAGACTTCAAATAA
```

SAR0146 (Strain MRSA252)

(SEQ ID NO: 11)

```
MKNIYKSLTVSAIVATVSLSALPQSLAITHESQPTKQQQTVLFDRSHGQT
AGAADWVSDGAFSDYADSIQKQGYDVKAIDGHSNITEASLKSSKIFVIPE
ANIPFKESEQAAIVNYVKQGGNVVFISDHYNADRNLNRIDSSEAMNGYRR
GAYEDMSKGMNAEEKSSTAMQGVKSSDWLSTNFGVRFRYNALGDLNTSNI
VSSKESFGITEGVKSVSMHAGSTLAITNPEKAKGIVYTPEQLPAKSKWSH
AVDQGIYNGGGKAEGPYVAISKVGKGKAAFIGDSSLVEDSSPKYVREDNG
EKKKTYDGFKEQDNGKLLNNITAWMSKDNDGKSLKASGLTLDTKTKLLDF
ERPERSTEPEKEPWSQPPSGYKWYDPTTFKAGSYGSEKGADPQPNTPDDH
TPPNQTEKVSFDIPQNVSVNEPFEVTIHLKGFEANQTLENLRVGIYKEGG
```

RQIGQFSSKDNDYNPPGYSTLPTVKADENGNATIKVNAKVLESMEGSKIR

LKLGDKTLITTDFK

SAR0146 (Strain MRSA252) Nucleic acid sequence
(SEQ ID NO: 12)
ATGAAAAATATATATAAGTCATTAACTGTCTCTGCAATTGTTGCAACGGT

ATCATTAAGTGCTTTACCGCAATCTTTAGCTATAACGCATGAATCGCAAC

CTACAAAGCAACAGCAAACAGTATTATTCGATCGTTCTCATGGTCAAACA

GCTGGTGCTGCAGATTGGGTTAGTGATGGTGCATTTTCAGATTATGCGGA

TTCAATACAAAAACAAGGTTATGACGTTAAAGCTATTGATGGTCATTCGA

ACATAACAGAAGCAAGTTTGAAAAGTTCCAAAATATTTGTAATTCCTGAG

GCTAACATTCCTTTCAAAGAATCAGAACAGGCAGCAATTGTTAACTATGT

GAAACAAGGGGGAAATGTTGTCTTTATTTCAGACCATTACAATGCTGACC

GAAATTTAAATCGTATTGATTCATCAGAGGCAATGAATGGTTATCGACGT

GGAGCGTATGAAGATATGTCGAAAGGTATGAATGCAGAAGAAAAAGTTC

TACTGCAATGCAAGGTGTGAAAAGTTCAGATTGGTTATCTACAAACTTTG

GCGTACGTTTTCGATATAATGCACTAGGTGATTTAAATACGAGCAATATT

GTTTCTTCAAAAGAAAGTTTTGGTATTACTGAAGGTGTGAAATCTGTATC

TATGCATGCCGGTTCGACATTAGCAATTACTAATCCAGAGAAAGCAAAAG

GTATTGTGTATACACCAGAACAATTGCCAGCGAAAAGTAAATGGTCACAT

GCTGTAGATCAAGGTATTTATAATGGGGGCGGTAAAGCAGAAGGTCCCTA

TGTAGCAATTTCTAAAGTTGGAAAAGGTAAAGCAGCATTTATCGGTGATT

CATCACTTGTGGAAGATAGTTCGCCCAAATATGTGAGAGAAGATAATGGA

GAAAAGAAGAAAACATATGATGGTTTTAAAGAACAAGACAACGGTAAGCT

ATTAAATAATATAACAGCTTGGATGTCTAAAGATAATGATGGGAAATCAC

TTAAGGCGAGTGGCCTAACATTAGATACAAAGACTAAGTTGCTTGATTTT

GAACGACCAGAGCGTTCAACTGAGCCTGAAAAAGAGCCATGGTCACAACC

GCCGAGTGGTTATAAATGGTATGACCCAACAACATTTAAAGCAGGTAGTT

ATGGCAGTGAAAAAGGCGCGGATCCTCAGCCAAACACACCAGATGATCAT

ACGCCACCAAATCAGACCGAAAAAGTATCATTTGATATCCCGCAAAATGT

TTCTGTAAATGAGCCATTTGAAGTGACAATACATTTAAAAGGATTTGAAG

CAAATCAAACACTTGAAAATCTTAGAGTTGGTATTTACAAAGAAGGAGGA

CGTCAAATCGGACAATTTTCAAGTAAAGATAACGATTATAACCCGCCAGG

TTACAGTACTTTGCCAACAGTTAAAGCAGATGAAAACGGAAATGCCACAA

TTAAGGTCAATGCCAAAGTACTCGAAAGTATGGAAGGTTCAAAGATTCGT

TTAAAACTCGGTGACAAAACCTTGATTACAACAGACTTCAAATAA

The following Table 1.0 shows the homology of the proteins of the present invention, namely SEQ ID NOS 1, 3, 5, 7, 9, and 11 as set forth above.

Table 1.0

```
AA_MULTIPLE_ALIGNMENT 1.0
MSF:    514                         Type: 2
Name:  MW0118(Strain_MW2)           Len: 514   Check: 1153   Weight: 1.0
Name:  SAS0118_(Strain_MSSA476)     Len: 514   Check: 1153   Weight: 1.0
Name:  SA0139_(Strain_N315)         Len: 514   Check:  332   Weight: 1.0
Name:  SACOL0129_(Strain_COL)       Len: 514   Check: 1452   Weight: 1.0
Name:  SAV0144_(Strain_Mu50)        Len: 514   Check:  332   Weight: 1.0
Name:  SAR0146_(Strain_MRSA252)     Len: 514   Check:  508   Weight: 1.0

1                                                    50
MW0118(Strain_MW2)             MKKIYKSLTV  SAIVATVSLS  ALPQSLAITH  ESQPTKQQRT  VLFDRSHGQT
SAS0118_(Strain_MSSA476)       MKKIYKSLTV  SAIVATVSLS  ALPQSLAITH  ESQPTKQQRT  VLFDRSHGQT
SA0139_(Strain_N315)           MKKIYKSLTV  SAIVATVSLS  ALPQSLAITH  ESQPTKQQRT  VLFDRSHGQT
SACOL0129_(Strain_COL)         MKKIYKSLTV  SAIVATVSLS  ALPQSLAITH  ESQPTKQQRT  VLFDRSHGQT
SAV0144_(Strain_Mu50)          MKKIYKSLTV  SAIVATVSLS  ALPQSLAITH  ESQPTKQQRT  VLFDRSHGQT
SAR0146_(Strain_MRSA252)       MKNIYKSLTV  SAIVATVSLS  ALPQSLAITH  ESQPTKQQQT  VLFDRSHGQT 51                                                   100
MW0118(Strain_MW2)             AGAADWVSDG  AFSDYADSIQ  KQGYDVKAID  GHSNITEASL  KSSKIFVIPE
SAS0118_(Strain_MSSA476)       AGAADWVSDG  AFSDYADSIQ  KQGYDVKAID  GHSNITEASL  KSSKIFVIPE
SA0139_(Strain_N315)           AGAADWVSDG  AFSDYADSIQ  KQGYDVKAID  GHSNITEASL  KSSKIFVIPE
SACOL0129_(Strain_COL)         AGAADWVSDG  AFSDYADSIQ  KQGYDVKAID  GHSNITEASL  MSSKIFVIPE
SAV0144_(Strain_Mu50)          AGAADWVSDG  AFSDYADSIQ  KQGYDVKAID  GHSNITEASL  KSSKIFVIPE
SAR0146_(Strain_MRSA252)       AGAADWVSDG  AFSDYADSIQ  KQGYDVKAID  GHSNITEASL  KSSKIFVIPE 101                                                  150
MW0118(Strain_MW2)             ANIPFKESEQ  AAIVNYVKQG  GNVVFISDHY  NADRNLNRID  SSEAMNGYRR
SAS0118_(Strain_MSSA476)       ANIPFKESEQ  AAIVNYVKQG  GNVVFISDHY  NADRNLNRID  SSEAMNGYRR
SA0139_(Strain_N315)           ANIPFKESEQ  AAIVNYVKQG  GNVVFISDHY  NADRNLNRID  SSEAMNGYRR
SACOL0129_(Strain_COL)         ANIPFKESEQ  AAIVKYVKQG  GNVVFISDHY  NADRNLNRID  SSEAMNGYRR
SAV0144_(Strain_Mu50)          ANIPFKESEQ  AAIVNYVKQG  GNVVFISDHY  NADRNLNRID  SSEAMNGYRR
SAR0146_(Strain_MRSA252)       ANIPFKESEQ  AAIVNYVKQG  GNVVFISDHY  NADRNLNRID  SSEAMNGYRR 151                                                  200
MW0118(Strain_MW2)             GAYEDMSKGM  NAEEKSSTAM  QGVKSSDWLS  TNFGVRFRYN  ALGDLNTSNI
SAS0118_(Strain_MSSA476)       GAYEDMSKGM  NAEEKSSTAM  QGVKSSDWLS  TNFGVRFRYN  ALGDLNTSNI
SA0139_(Strain_N315)           GAYEDMSKGM  NAEEKSSTAM  QGVKSSDWLS  TNFGVRFRYN  ALGDLNTSNI
SACOL0129_(Strain_COL)         GAYEDMSKGM  NAEENSSTAM  QGVKSSDWLS  TNFGVRFRYN  ALGDLNTSNI
SAV0144_(Strain_Mu50)          GAYEDMSKGM  NAEEKSSTAM  QGVKSSDWLS  TNFGVRFRYN  ALGDLNTSNI
SAR0146_(Strain_MRSA252)       GAYEDMSKGM  NAEEKSSTAM  QGVKSSDWLS  TNFGVRFRYN  ALGDLNTSNI
```

Table 1.0-continued

```
                              201                                                      250
MW0118(Strain_MW2)            VSSKESFGIT EGVKSVSMHA GSTLAITNPE KAKGIVYTPE QLPAKSKWSH
SAS0118_(Strain_MSSA476)      VSSKESFGIT EGVKSVSMHA GSTLAITNPE KAKGIVYTPE QLPAKSKWSH
SA0139_(Strain_N315)          VSSKESFGIT EGVKSVSMHA GSTLAITNPE KAKGIVYTPE QLPAKSKWSH
SACOL0129_(Strain_COL)        VSSKESFGIT EGVKSVSMHA GSTLAITNPE KAKGIVYTPE QLPAKSKWSH
SAV0144_(Strain_Mu50)         VSSKESFGIT EGVKSVSMHA GSTLAITNPE KAKGIVYTPE QLPAKSKWSH
SAR0146_(Strain_MRSA252)      VSSKESFGIT EGVKSVSMHA GSTLAITNPE KAKGIVYTPE QLPAKSKWSH 251                                                      300
MW0118(Strain_MW2)            AVDQGIYNGG GKAEGPYVAI SKVGKGKAAF IGDSSLVEDS SPKYVREDNG
SAS0118_(Strain_MSSA476)      AVDQGIYNGG GKAEGPYVAI SKVGNGKAAF IGDSSLVEDS SPKYVREDNG
SA0139_(Strain_N315)          AVDQGIYNGG GKAEGPYVAI SKVGKGKAAF IGDSSLVEDS SPKYVREDNG
SACOL0129_(Strain_COL)        AVDQGIYNGG GKAEGPYVAI SKVGKGKAAF IGDSSLVEDS SPKYVREDNG
SAV0144_(Strain_Mu50)         AVDQGIYNGG GKAEGPYVAI SKVGKGKAAF IGDSSLVEDS SPKYVREDNG
SAR0146_(Strain_MRSA252)      AVDQGIYNGG GKAEGPYVAI SKVGKGKAAF IGDSSLVEDS SPKYVREDNG 301                                                      350
MW0118(Strain_MW2)            EKKKTYDGFK EQDNGKLLNN ITDWMSKDSD GKSLKASGLT LDTKTKLLDF
SAS0118_(Strain_MSSA476)      EKKKTYDGFK EQDNGKLLNN ITDWMSKDSD GKSLKASGLT LDTKTKLLDF
SA0139_(Strain_N315)          EKKKTYDGFK EQDNGKLLNN ITAWMSKDSD GKSLKASGLT LDTKTKLLDF
SACOL0129_(Strain_COL)        EKKKTYDGFK EQDNGKLLNN ITAWMSKDND GKSLKASSLT LDTKTKLLDF
SAV0144_(Strain_Mu50)         EKKKTYDGFK EQDNGKLLNN ITAWMSKDSD GKSLKASGLT LDTKTKLLDF
SAR0146_(Strain_MRSA252)      EKKKTYDGFK EQDNGKLLNN ITAWMSKDND GKSLKASGLT LDTKTKLLDF 351                                                      400
MW0118(Strain_MW2)            ERPERSTEPE KEPWSQPPSG YKWYDPTTFK AGSYGSEKGA DPQPNTPDDH
SAS0118_(Strain_MSSA476)      ERPERSTEPE KEPWSQPPSG YKWYDPTTFK AGSYGSEKGA DPQPNTPDDH
SA0139_(Strain_N315)          ERPERSTEPE KEPWSQPPSG YKWYDPTTFK AGSYGSEKGA DPQPNTPDDH
SACOL0129_(Strain_COL)        ERPERSTEPE KEPWSQPPSG YKWYDPTTFK AGSYGSEKGA DPQPNTPDDH
SAV0144_(Strain_Mu50)         ERPERSTEPE KEPWSQPPSG YKWYDPTTFK AGSYGSEKGA DPQPNTPDDH
SAR0146_(Strain_MRSA252)      ERPERSTEPE KEPWSQPPSG YKWYDPTTFK AGSYGSEKGA DPQPNTPDDH 401                                                      450
MW0118(Strain_MW2)            TPPNQNEKVT FDIPQNVSVN EPFEMTIHLK GFEANQTLEN LRVGIYKEGG
SAS0118_(Strain_MSSA476)      TPPNQNEKVT FDIPQNVSVN EPFEMTIHLK GFEANQTLEN LRVGIYKEGG
SA0139_(Strain_N315)          TPPNQNVKIS FDIPQNVSVN EPFEVTIHLK GFEANQTLEN LRVGIYKEGG
SACOL0129_(Strain_COL)        TPPNQNEKVT FDIPQNVSVN EPFEMTIHLK GFEANQTLEN LRVGIYKEGG
SAV0144_(Strain_Mu50)         TPPNQNVKIS FDIPQNVSVN EPFEVTIHLK GFEANQTLEN LRVGIYKEGG
SAR0146_(Strain_MRSA252)      TPPNQTEKVS FDIPQNVSVN EPFEVTIHLK GFEANQTLEN LRVGIYKEGG 451                                                      500
MW0118(Strain_MW2)            RQIGQFSSKD NDYNPPGYST LPTVKADENG NVTIKVNAKV LESMEGSKIR
SAS0118_(Strain_MSSA476)      RQIGQFSSKD NDYNPPGYST LPTVKADENG NVTIKVNAKV LESMEGSKIR
SA0139_(Strain_N315)          RQIGQFSSKD NDYNPPGYST LPTVKADENG NATIKINAKV LESMEGSKIR
SACOL0129_(Strain_COL)        RQIGQFSSKD NDYNPPGYST LPTVKADENG NVTIKVNAKV LESMEGSKIR
SAV0144_(Strain_Mu50)         RQIGQFSSKD NDYNPPGYST LPTVKADENG NATIKINAKV LESMEGSKIR
SAR0146_(Strain_MRSA252)      RQIGQFSSKD NDYNPPGYST LPTVKADENG NATIKVNAKV LESMEGSKIR 501        514
MW0118(Strain_MW2)            LKLGDKTLIT TDFK
SAS0118_(Strain_MSSA476)      LKLGDKTLIT TDFK
SA0139_(Strain_N315)          LKLGDKTLIT TDFK
SACOL0129_(Strain_COL)        LKLGDKTLIT TDFK
SAV0144_(Strain_Mu50)         LKLGDKTLIT TDFK
SAR0146_(Strain_MRSA252)      LKLGDKTLIT TDFK
```

In addition to the homology of proteins of Table 1.0, FIGS. 4A-4C depict a sequence alignment showing proteins in accordance with the invention, along with a consensus sequence.

In summary, the present invention provides novel MSCRAMM® proteins from S. aureus which are putative highly-expressed antigens from methicillin-resistant S. aureus, including community-associated MRSA (CA-MRSA), and these antigens can thus be utilized in methods of generating antibodies capable of binding these antigens which can be useful in methods of treating or preventing infection from MRSA. The present invention thus is directed to these proteins, antibodies capable of binding these proteins, methods of generating said antibodies, nucleic acids coding for said proteins, and pharmaceutical compositions or vaccines which include the proteins or antibodies of the present invention in combination with a pharmaceutically acceptable vehicle, carrier or excipient.

The following example is provided which exemplifies aspects of the preferred embodiments of the present invention. It should be appreciated by those of skill in the art that the techniques disclosed in the example which follows represents techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE

Most CA MRSA strains produce a toxin called Panton-Valentine Leukocidin and the presence of this toxin has been associated with enhanced binding to extracellular matrix components. Based on our experimental data, we can show that PVL-positive CA-MRSA strains have an altered protein expression profile that results in the over-expression of cell surface adhesins giving these strains an advantage in their ability to invade and colonize the mammalian host. As the presence of the pvl locus appears to alter the expression profile of these bacterial strains, the global gene expression of PVL-negative (FIG. 1, lanes 1 and 2) and PVL-positive strains (FIG. 1, lane 3) was compared. To correlate the transcriptional profiles with our protein expression data (FIG. 1), we harvested total bacterial RNA from both strains at exponential and stationary phases. When compared to the PVL-negative strain, 88 genes show a different expression in the PVL-positive strain during logarithmic growth, whereas during the stationary phase, 673 genes show differential expression in the PVL-positive strain. A small group of differentially expressed genes, relevant to the focus of this proposal, is shown in FIG. 2. One of the most up-regulated genes in PVL-positive strains is a novel MSCRAMM® designated as MW0118 in the *Staphylococcus aureus* MW2 strain (SAS0118 in strain MSSA476, SACOL0129 in strain COL, SA0139 in strain N315, SAV0144 in strain Mu50, and SAR0146 in strain MRSA252), and microarray analyses revealed the overexpression of MW0118 in a PVL+ strain.

We have now determined that MW0118 is a previously unidentified putative cell wall anchored protein with MSCRAMM® characteristics (FIG. 3) which is highly expressed in PVL+, CA MRSA strains. Additionally, we have determined that:

The expression of MW0118 may increase the virulence of CA MRSA strains;

Defined regions in MW0118 can be expressed as recombinant proteins to generate antibodies that block ligand binding;

Defined regions in MW0118 can therefore be used as vaccines;

Antibodies (polyclonal or monoclonal antibodies) can be generated against MW0118 that may interfere with the CA MRSA colonization and virulence; and Antibodies (polyclonal or monoclonal antibodies) can be raised against MW0118 that be used as therapies against *S. aureus* infections.

Accordingly, the invention is directed to the novel MSCRAMM® designated as MW0118 in the *Staphylococcus aureus* MW2 strain (as well as to its homologues SAS0118 in strain MSSA476, SACOL0129 in strain COL, SA0139 in strain N315, SAV0144 in strain Mu50, and SAR0146 in strain MRSA252). In addition, the invention is directed to the nucleic acids coding for these proteins, as well as to monoclonal and polyclonal antibodies which recognize these proteins. Finally, the invention is directed to methods of prevention and treatment of *S. aureus* infection using MW0118 or its homologues, nucleic acids coding for said proteins, or antibodies recognizing said proteins.

Our evidence shows that the protein designated as MW0118 constitutes a novel virulence factor encoded by PVL+ CA MRSA. The increased expression of this protein had never been detected. The use of polyclonal or monoclonal antibodies reacting with MW0118 constitutes a new strategy for the prevention and treatment of infections caused by *S. aureus*. An analogous strategy, using antibodies targeted to the MSCRAMM® ClfA, has been effective in animal models for the treatment and prevention of infections caused by *S. aureus*. The MW0118 has been cloned, and can be expressed in *E. coli*, and protective monoclonal and polyclonal antibodies can be generated against it. MW0118 and its homologues have been isolated sequenced as indicated above, both with regard to protein and nucleic acid sequences.

In terms of methods of treating *S. aureus*, infections caused by *S. aureus* are generally difficult to treat, because these organisms are resistant to multiple antibiotics, and can form biofilms on the surface of the indwelling medical devices they infect. In accordance with the invention, MW0118 or its homologues may be used as an immunogen to constitute an excellent preparation to develop therapies to treat and prevent CA MRSA infections because these protein may be an important, unique virulence factor. The advantage of using MW0118 and antibodies generated against the MW0118 as a treatment strategy for the prevention of *S. aureus* infections is that the humanized antibodies are very effective and do not cause secondary adverse reactions. This is a significant improvement over the antibiotic therapies that can be toxic to the host at high or prolonged doses and are ineffective in the necrotizing pneumonia cases.

The present invention thus outlines how to generate effective polyclonal and monoclonal antibodies for the prevention and treatment of infections caused by CA MRSA and related organisms. The populations of patients at risk are large and well defined: including healthy school-age children and young adults. An immunotherapeutic strategy is advantageous in these populations because the morbidity and mortality associated with hematogenously disseminated bacteremia and necrotizing pneumonia remains high, even with currently available antibiotic therapy. In addition, an increasing number of antibiotic-resistant strains is emerging, associated with the overuse of antibiotic agents, justifying the development of alternative and complementary therapeutic strategies. In accordance with the present invention, peptides or recombinant proteins that contain the active site(s) on MW0118 responsible for their extracellular matrix binding properties are included in the invention along with the use of these peptides or recombinant proteins as means of preventing *S. aureus* attachment to the host tissues.

What is claimed is:

1. An isolated antigen from methicillin-resistant *Staphylococcus aureus* (MRSA) comprising a protein having the amino acid sequence of SEQ ID NO: 11.

2. A composition comprising the antigen of claim 1 and a pharmaceutically acceptable vehicle, excipient or carrier.

3. A composition comprising an immunogenic amount of the antigen of claim 1 and a pharmaceutically acceptable vehicle, excipient or carrier.

4. The antigen of claim 1, wherein said antigen is encoded by a nucleic acid having the sequence of SEQ ID NO: 12, or degenerates thereof.

5. A method of generating an immunogenic response comprising administering to a human or animal an immunogenic amount of the antigen of claim 1.

* * * * *

SEQUENCE LISTING

<160> NUMBER OF SEQ ID NOS: 12

<210> SEQ ID NO 1
<211> LENGTH: 514
<212> TYPE: PRT
<213> ORGANISM: Staphylococcus aureus (Strain MW2)

<400> SEQUENCE: 1

Met Lys Lys Ile Tyr Lys Ser Leu Thr Val Ser Ala Ile Val Ala Thr
1               5                   10                  15

```
Val Ser Leu Ser Ala Leu Pro Gln Ser Leu Ala Ile Thr His Glu Ser
            20                  25                  30

Gln Pro Thr Lys Gln Gln Arg Thr Val Leu Phe Asp Arg Ser His Gly
        35                  40                  45

Gln Thr Ala Gly Ala Ala Asp Trp Val Ser Asp Gly Ala Phe Ser Asp
    50                  55                  60

Tyr Ala Asp Ser Ile Gln Lys Gln Gly Tyr Asp Val Lys Ala Ile Asp
 65                  70                  75                  80

Gly His Ser Asn Ile Thr Glu Ala Ser Leu Lys Ser Lys Ile Phe
                85                  90                  95

Val Ile Pro Glu Ala Asn Ile Pro Phe Lys Glu Ser Glu Gln Ala Ala
            100                 105                 110

Ile Val Asn Tyr Val Lys Gln Gly Gly Asn Val Val Phe Ile Ser Asp
        115                 120                 125

His Tyr Asn Ala Asp Arg Asn Leu Asn Arg Ile Asp Ser Ser Glu Ala
    130                 135                 140

Met Asn Gly Tyr Arg Arg Gly Ala Tyr Glu Asp Met Ser Lys Gly Met
145                 150                 155                 160

Asn Ala Glu Glu Lys Ser Ser Thr Ala Met Gln Gly Val Lys Ser Ser
                165                 170                 175

Asp Trp Leu Ser Thr Asn Phe Gly Val Arg Phe Arg Tyr Asn Ala Leu
            180                 185                 190

Gly Asp Leu Asn Thr Ser Asn Ile Val Ser Ser Lys Glu Ser Phe Gly
        195                 200                 205

Ile Thr Glu Gly Val Lys Ser Val Ser Met His Ala Gly Ser Thr Leu
    210                 215                 220

Ala Ile Thr Asn Pro Glu Lys Ala Lys Gly Ile Val Tyr Thr Pro Glu
225                 230                 235                 240

Gln Leu Pro Ala Lys Ser Lys Trp Ser His Ala Val Asp Gln Gly Ile
                245                 250                 255

Tyr Asn Gly Gly Gly Lys Ala Glu Gly Pro Tyr Val Ala Ile Ser Lys
            260                 265                 270

Val Gly Lys Gly Lys Ala Ala Phe Ile Gly Asp Ser Ser Leu Val Glu
        275                 280                 285

Asp Ser Ser Pro Lys Tyr Val Arg Glu Asp Asn Gly Glu Lys Lys Lys
    290                 295                 300

Thr Tyr Asp Gly Phe Lys Glu Gln Asp Asn Gly Lys Leu Leu Asn Asn
305                 310                 315                 320

Ile Thr Asp Trp Met Ser Lys Asp Ser Gly Lys Ser Leu Lys Ala
                325                 330                 335

Ser Gly Leu Thr Leu Asp Thr Lys Thr Lys Leu Leu Asp Phe Glu Arg
            340                 345                 350

Pro Glu Arg Ser Thr Glu Pro Glu Lys Glu Pro Trp Ser Gln Pro Pro
        355                 360                 365

Ser Gly Tyr Lys Trp Tyr Asp Pro Thr Thr Phe Lys Ala Gly Ser Tyr
    370                 375                 380

Gly Ser Glu Lys Gly Ala Asp Pro Gln Pro Asn Thr Pro Asp Asp His
385                 390                 395                 400

Thr Pro Pro Asn Gln Asn Glu Lys Val Thr Phe Asp Ile Pro Gln Asn
                405                 410                 415

Val Ser Val Asn Glu Pro Phe Glu Met Thr Ile His Leu Lys Gly Phe
            420                 425                 430

Glu Ala Asn Gln Thr Leu Glu Asn Leu Arg Val Gly Ile Tyr Lys Glu
        435                 440                 445
```

```
Gly Gly Arg Gln Ile Gly Gln Phe Ser Ser Lys Asp Asn Asp Tyr Asn
        450                 455                 460

Pro Pro Gly Tyr Ser Thr Leu Pro Thr Val Lys Ala Asp Glu Asn Gly
465                 470                 475                 480

Asn Val Thr Ile Lys Val Asn Ala Lys Val Leu Glu Ser Met Glu Gly
                485                 490                 495

Ser Lys Ile Arg Leu Lys Leu Gly Asp Lys Thr Leu Ile Thr Thr Asp
            500                 505                 510

Phe Lys

<210> SEQ ID NO 2
<211> LENGTH: 1545
<212> TYPE: DNA
<213> ORGANISM: Staphylococcus aureus (Strain MW2)

<400> SEQUENCE: 2
atgaaaaaaa tatataagtc attaactgtc tctgcaattg ttgcaacggt atcattaagt        60
gctttaccgc aatctttagc tataacgcat gaatcgcaac ctacaaagca acagcgaacg       120
gtattattcg atcgttctca tggtcaaaca gctggtgctg cagattgggt tagtgatggt       180
gcattttcag attatgcgga ttcaatacaa aaacaaggtt atgacgttaa agctattgat       240
ggtcattcga acataacaga agcaagtttg aaaagttcta aatatttcgt aattcctgag       300
gctaatattc ctttcaaaga atcagaacag gcagcaattg ttaactatgt gaaacaaggt       360
ggcaatgttg tctttatttc agatcattac aatgctgacc gaaatttaaa tcgtattgat       420
tcatcagagg caatgaatgg ttatcgacgt ggagcatatg aagatatgtc gaaaggtatg       480
aatgcagaag aaaaaagttc tactgcaatg caaggtgtga aagttcaga ttggttatct        540 acaaactttg gcgtacgttt tcgatataat gcactaggtg atttaaatac gagcaatatt       600
gtttcttcaa aagagagttt cggtattact gaaggtgtga atctgtctc tatgcatgcc        660 ggatcaacat tagcaattac taatccagag aaagcaaaag gtattgtgta tacaccagaa       720
caattgccag cgaaaagtaa atggtcacat gctgtagatc aaggtattta taatgggggc       780
ggtaaagcag aaggccccta tgtagcaatt tctaaagttg aaaaggtaa agcagcattt       840 atcggtgatt catcacttgt ggaagatagt tcgcccaaat atgtaagaga agataatgga       900
gaaaagaaga aaacatatga tggttttaaa gaacaagaca acggtaagct attaaataat       960
ataacggatt ggatgtctaa agatagtgat gggaaatcac ttaaggcgag tggactaaca      1020
ttagatacaa agactaagtt gcttgatttt gaacgaccag agcgttcaac tgagcctgaa      1080
aaagagccat ggtcacaacc gccgagtggt tataaatggt atgatccaac aacatttaaa      1140
gcaggtagtt atggcagcga aaaaggcgca gatcctcagc caaacacacc agatgatcat      1200
acgccaccaa atcagaacga aaagtaaca tttgatatcc cgcaaaatgt ttctgtaaat       1260
gagccatttg aaatgacaat acatttaaaa ggatttgaag caaatcaaac acttgaaaat      1320
cttagagttg gtatttacaa agaaggcgga cgtcaaatcg acaattttc aagtaaagat       1380 aacgattata cccaccagg ttacagtact ttgccaacag ttaaagcaga tgaaaacgga       1440
aatgtcacaa ttaaggtcaa tgctaaagta cttgaaagta tggaaggttc aaagattcgt      1500
ttaaaactcg gtgacaaaac cttgattaca acagacttca aataa                      1545

<210> SEQ ID NO 3
<211> LENGTH: 514
<212> TYPE: PRT
<213> ORGANISM: Staphylococcus aureus (Strain MSSA476)
```

-continued

<400> SEQUENCE: 3

```
Met Lys Lys Ile Tyr Lys Ser Leu Thr Val Ser Ala Ile Val Ala Thr
1               5                   10                  15

Val Ser Leu Ser Ala Leu Pro Gln Ser Leu Ala Ile Thr His Glu Ser
            20                  25                  30

Gln Pro Thr Lys Gln Gln Arg Thr Val Leu Phe Asp Arg Ser His Gly
        35                  40                  45

Gln Thr Ala Gly Ala Ala Asp Trp Val Ser Asp Gly Ala Phe Ser Asp
    50                  55                  60

Tyr Ala Asp Ser Ile Gln Lys Gln Gly Tyr Asp Val Lys Ala Ile Asp
65                  70                  75                  80

Gly His Ser Asn Ile Thr Glu Ala Ser Leu Lys Ser Ser Lys Ile Phe
                85                  90                  95

Val Ile Pro Glu Ala Asn Ile Pro Phe Lys Glu Ser Glu Gln Ala Ala
            100                 105                 110

Ile Val Asn Tyr Val Lys Gln Gly Gly Asn Val Val Phe Ile Ser Asp
        115                 120                 125

His Tyr Asn Ala Asp Arg Asn Leu Asn Arg Ile Asp Ser Ser Glu Ala
    130                 135                 140

Met Asn Gly Tyr Arg Arg Gly Ala Tyr Glu Asp Met Ser Lys Gly Met
145                 150                 155                 160

Asn Ala Glu Glu Lys Ser Ser Thr Ala Met Gln Gly Val Lys Ser Ser
                165                 170                 175

Asp Trp Leu Ser Thr Asn Phe Gly Val Arg Phe Arg Tyr Asn Ala Leu
            180                 185                 190

Gly Asp Leu Asn Thr Ser Asn Ile Val Ser Ser Lys Glu Ser Phe Gly
        195                 200                 205

Ile Thr Glu Gly Val Lys Ser Val Ser Met His Ala Gly Ser Thr Leu
    210                 215                 220

Ala Ile Thr Asn Pro Glu Lys Ala Lys Gly Ile Val Tyr Thr Pro Glu
225                 230                 235                 240

Gln Leu Pro Ala Lys Ser Lys Trp Ser His Ala Val Asp Gln Gly Ile
                245                 250                 255

Tyr Asn Gly Gly Gly Lys Ala Glu Gly Pro Tyr Val Ala Ile Ser Lys
            260                 265                 270

Val Gly Lys Gly Lys Ala Ala Phe Ile Gly Asp Ser Ser Leu Val Glu
        275                 280                 285

Asp Ser Ser Pro Lys Tyr Val Arg Glu Asp Asn Gly Glu Lys Lys Lys
    290                 295                 300

Thr Tyr Asp Gly Phe Lys Glu Gln Asp Asn Gly Lys Leu Leu Asn Asn
305                 310                 315                 320

Ile Thr Asp Trp Met Ser Lys Asp Ser Asp Gly Lys Ser Leu Lys Ala
                325                 330                 335

Ser Gly Leu Thr Leu Asp Thr Lys Thr Lys Leu Leu Asp Phe Glu Arg
            340                 345                 350

Pro Glu Arg Ser Thr Glu Pro Glu Lys Glu Pro Trp Ser Gln Pro Pro
        355                 360                 365

Ser Gly Tyr Lys Trp Tyr Asp Pro Thr Phe Lys Ala Gly Ser Tyr
    370                 375                 380

Gly Ser Glu Lys Gly Ala Asp Pro Gln Pro Asn Thr Pro Asp Asp His
385                 390                 395                 400

Thr Pro Pro Asn Gln Asn Glu Lys Val Thr Phe Asp Ile Pro Gln Asn
                405                 410                 415
```

Val Ser Val Asn Glu Pro Phe Glu Met Thr Ile His Leu Lys Gly Phe
            420                 425                 430

Glu Ala Asn Gln Thr Leu Glu Asn Leu Arg Val Gly Ile Tyr Lys Glu
        435                 440                 445

Gly Gly Arg Gln Ile Gly Gln Phe Ser Ser Lys Asp Asn Asp Tyr Asn
    450                 455                 460

Pro Pro Gly Tyr Ser Thr Leu Pro Thr Val Lys Ala Asp Glu Asn Gly
465                 470                 475                 480

Asn Val Thr Ile Lys Val Asn Ala Lys Val Leu Glu Ser Met Glu Gly
            485                 490                 495

Ser Lys Ile Arg Leu Lys Leu Gly Asp Lys Thr Leu Ile Thr Thr Asp
            500                 505                 510

Phe Lys

<210> SEQ ID NO 4
<211> LENGTH: 1545
<212> TYPE: DNA
<213> ORGANISM: Staphylococcus aureus (Strain MSSA476)

<400> SEQUENCE: 4

```
atgaaaaaaa tatataagtc attaactgtc tctgcaattg ttgcaacggt atcattaagt     60
gctttaccgc aatctttagc tataacgcat gaatcgcaac ctacaaagca acagcgaacg    120
gtattattcg atcgttctca tggtcaaaca gctggtgctg cagattgggt tagtgatggt    180
gcattttcag attatgcgga ttcaatacaa aaacaaggtt atgacgttaa agctattgat    240
ggtcattcga acataacaga agcaagtttg aaaagttcta aatatttgt aattcctgag    300
gctaatattc ctttcaaaga atcagaacag gcagcaattg ttaactatgt gaaacaaggt    360
ggcaatgttg tctttatttc agatcattac aatgctgacc gaaatttaaa tcgtattgat    420
tcatcagagg caatgaatgg ttatcgacgt ggagcatatg aagatatgtc gaaaggtatg    480
aatgcagaag aaaaaagttc tactgcaatg caaggtgtga aaagttcaga ttggttatct    540
acaaactttg gcgtacgttt tcgatataat gcactaggtg atttaaatac gagcaatatt    600
gtttcttcaa aagagagttt cggtattact gaaggtgtga atctgtctc tatgcatgcc    660
ggatcaacat tagcaattac taatccagag aaagcaaaag gtattgtgta tacaccagaa    720
caattgccag cgaaaagtaa atggtcacat gctgtagatc aaggtattta taatggggc    780
ggtaaagcag aaggccccta tgtagcaatt tctaaagttg aaaaggtaa agcagcattt    840
atcggtgatt catcacttgt ggaagatagt tcgcccaaat atgtaagaga agataatgga    900
gaaaagaaga aaacatatga tggttttaaa gaacaagaca acggtaagct attaaataat    960
ataacggatt ggatgtctaa agatagtgat gggaaatcac ttaaggcgag tggactaaca   1020
ttagatacaa agactaagtt gcttgatttt gaacgaccag agcgttcaac tgagcctgaa   1080
aaagagccat ggtcacaacc gccgagtggt tataaatggt atgatccaac acatttaaa    1140
gcaggtagtt atggcagcga aaaggcgca gatcctcagc caaacacacc agatgatcat   1200
acgccaccaa atcagaacga aaagtaaca tttgatatcc cgcaaaatgt ttctgtaaat   1260
gagccatttg aaatgacaat acatttaaaa ggatttgaag caaatcaaac acttgaaaat   1320
cttagagttg gtatttacaa agaaggcgga cgtcaaatcg gacaattttc aagtaaagat   1380
aacgattata acccaccagg ttacagtact ttgccaacag ttaaagcaga tgaaaacgga   1440
aatgtcacaa ttaaggtcaa tgctaaagta cttgaaagta tggaaggttc aaagattcgt   1500
ttaaaactcg gtgacaaaac cttgattaca acagacttca ataa                    1545
```

<210> SEQ ID NO 5
<211> LENGTH: 514
<212> TYPE: PRT
<213> ORGANISM: Staphylococcus aureus (Strain N315)

<400> SEQUENCE: 5

```
Met Lys Lys Ile Tyr Lys Ser Leu Thr Val Ser Ala Ile Val Ala Thr
1               5                   10                  15

Val Ser Leu Ser Ala Leu Pro Gln Ser Leu Ala Ile Thr His Glu Ser
            20                  25                  30

Gln Pro Thr Lys Gln Gln Arg Thr Val Leu Phe Asp Arg Ser His Gly
        35                  40                  45

Gln Thr Ala Gly Ala Ala Asp Trp Val Ser Asp Gly Ala Phe Ser Asp
    50                  55                  60

Tyr Ala Asp Ser Ile Gln Lys Gln Gly Tyr Asp Val Lys Ala Ile Asp
65                  70                  75                  80

Gly His Ser Asn Ile Thr Glu Ala Ser Leu Lys Ser Lys Ile Phe
                85                  90                  95

Val Ile Pro Glu Ala Asn Ile Pro Phe Lys Glu Ser Glu Gln Ala Ala
            100                 105                 110

Ile Val Asn Tyr Val Lys Gln Gly Gly Asn Val Val Phe Ile Ser Asp
        115                 120                 125

His Tyr Asn Ala Asp Arg Asn Leu Asn Arg Ile Asp Ser Ser Glu Ala
    130                 135                 140

Met Asn Gly Tyr Arg Arg Gly Ala Tyr Glu Asp Met Ser Lys Gly Met
145                 150                 155                 160

Asn Ala Glu Glu Lys Ser Ser Thr Ala Met Gln Gly Val Lys Ser Ser
                165                 170                 175

Asp Trp Leu Ser Thr Asn Phe Gly Val Arg Phe Arg Tyr Asn Ala Leu
            180                 185                 190

Gly Asp Leu Asn Thr Ser Asn Ile Val Ser Ser Lys Glu Ser Phe Gly
        195                 200                 205

Ile Thr Glu Gly Val Lys Ser Val Ser Met His Ala Gly Ser Thr Leu
    210                 215                 220

Ala Ile Thr Asn Pro Glu Lys Ala Lys Gly Ile Val Tyr Thr Pro Glu
225                 230                 235                 240

Gln Leu Pro Ala Lys Ser Lys Trp Ser His Ala Val Asp Gln Gly Ile
                245                 250                 255

Tyr Asn Gly Gly Gly Lys Ala Glu Gly Pro Tyr Val Ala Ile Ser Lys
            260                 265                 270

Val Gly Lys Gly Lys Ala Ala Phe Ile Gly Asp Ser Ser Leu Val Glu
        275                 280                 285

Asp Ser Ser Pro Lys Tyr Val Arg Glu Asp Asn Gly Glu Lys Lys Lys
    290                 295                 300

Thr Tyr Asp Gly Phe Lys Glu Gln Asp Asn Gly Lys Leu Leu Asn Asn
305                 310                 315                 320

Ile Thr Ala Trp Met Ser Lys Asp Ser Asp Gly Lys Ser Leu Lys Ala
                325                 330                 335

Ser Gly Leu Thr Leu Asp Thr Lys Thr Lys Leu Leu Asp Phe Glu Arg
            340                 345                 350

Pro Glu Arg Ser Thr Glu Pro Glu Lys Glu Pro Trp Ser Gln Pro Pro
        355                 360                 365

Ser Gly Tyr Lys Trp Tyr Asp Pro Thr Thr Phe Lys Ala Gly Ser Tyr
    370                 375                 380
```

Gly Ser Glu Lys Gly Ala Asp Pro Gln Pro Asn Thr Pro Asp His
385                 390                 395                 400

Thr Pro Pro Asn Gln Asn Val Lys Ile Ser Phe Asp Ile Pro Gln Asn
            405                 410                 415

Val Ser Val Asn Glu Pro Phe Glu Val Thr Ile His Leu Lys Gly Phe
            420                 425                 430

Glu Ala Asn Gln Thr Leu Glu Asn Leu Arg Val Gly Ile Tyr Lys Glu
            435                 440                 445

Gly Gly Arg Gln Ile Gly Gln Phe Ser Ser Lys Asp Asn Asp Tyr Asn
        450                 455                 460

Pro Pro Gly Tyr Ser Thr Leu Pro Thr Val Lys Ala Asp Glu Asn Gly
465                 470                 475                 480

Asn Ala Thr Ile Lys Ile Asn Ala Lys Val Leu Glu Ser Met Glu Gly
            485                 490                 495

Ser Lys Ile Arg Leu Lys Leu Gly Asp Lys Thr Leu Ile Thr Thr Asp
            500                 505                 510

Phe Lys

<210> SEQ ID NO 6
<211> LENGTH: 1545
<212> TYPE: DNA
<213> ORGANISM: Staphylococcus aureus (Strain N315)

<400> SEQUENCE: 6
atgaaaaaaa tatataagtc attaactgtc tctgcaattg ttgcaacggt atcattaagt      60
gctttaccgc aatctttagc tataacgcat gaatcgcaac ctacaaagca acagcgaacg     120
gtattattcg atcgttctca tggtcaaaca gctggtgctg cagattgggt tagtgatggt     180
gcattttcag attatgcgga ttcaatacaa aaacaaggtt atgacgttaa agctattgat     240
ggtcattcga acataacaga agcaagtttg aaaagttcca aatatttcgt aattcctgag     300
gctaacattc ctttcaaaga atcagaacag gcagcaattg ttaactatgt gaaacaaggt     360
ggcaatgttt tctttatttc agatcattac aatgctgacc gaaatttaaa tcgtattgat     420
tcatcggagg caatgaatgg ttatcgacgt ggagcatatg aagatatgtc gaaaggtatg     480
aatgcagaag aaaaaagctc tactgcaatg caaggtgtga aagttcaga ttggttatct      540
acaaactttg gcgtacgttt tcgatataat gcactaggtg atttaaatac gagcaatatt     600
gtttcttcaa agaaagtttt cggtattact gaaggtgtga atctgtctc tatgcatgcc      660
ggatcgacat tagcaattac taatccagag aaagcaaaag gtattgtgta tacaccagaa     720
caattgccag cgaaaagtaa atggtcacat gctgtagatc aaggtatttt aaatggtggc     780
ggtaaagcag aaggccccta tgtagcaatt tctaaagttg aaaaggtaa agcagcattt      840
atcggtgatt catcacttgt ggaagatagt tcgcccaaat atgtaagaga gataatgga      900
gaaaagaaga aaacatatga tggttttaaa gaacaagaca cgggtaagct attaaataat     960
ataacggctt ggatgtctaa agatagtgat gggaaatcac ttaaggcgag tggactaaca    1020
ttagatacaa agactaagtt gcttgatttt gaacgaccag agcgttcaac tgagcctgaa    1080
aaagagccat ggtcacaacc gccgagtggt tataaatggt atgacccaac aacatttaaa    1140
gcaggtagtt atggcagtga aaaggcgcg atcctcagc aaacacacc agatgatcat       1200
acgccaccaa atcagaacgt aaaaatatca tttgatatcc cgcaaaatgt ttctgtaaat    1260
gagccatttg aagtgacaat acatttaaaa ggatttgaag caaatcaaac acttgaaaat    1320
cttagagttg gtatttacaa agaaggcgga cgtcaaatcg acaattttc aagtaaagat    1380

```
aacgattata acccaccagg ttacagtact ttgccaacag ttaaagcaga tgaaaacgga    1440
aatgctacaa ttaagatcaa tgctaaagta cttgaaagta tggaaggttc aaagattcgt    1500
ttaaaactcg gtgacaaaac cttgattaca acagacttca aataa                    1545
```

<210> SEQ ID NO 7
<211> LENGTH: 514
<212> TYPE: PRT
<213> ORGANISM: Staphylococcus aureus (Strain COL)

<400> SEQUENCE: 7

```
Met Lys Lys Ile Tyr Lys Ser Leu Thr Val Ser Ala Ile Val Ala Thr
 1               5                  10                  15

Val Ser Leu Ser Ala Leu Pro Gln Ser Leu Ala Ile Thr His Glu Ser
             20                  25                  30

Gln Pro Thr Lys Gln Gln Arg Thr Val Leu Phe Asp Arg Ser His Gly
         35                  40                  45

Gln Thr Ala Gly Ala Ala Asp Trp Val Ser Asp Gly Ala Phe Ser Asp
     50                  55                  60

Tyr Ala Asp Ser Ile Gln Lys Gln Gly Tyr Asp Val Lys Ala Ile Asp
 65                  70                  75                  80

Gly His Ser Asn Ile Thr Glu Ala Ser Leu Lys Ser Lys Ile Phe
                 85                  90                  95

Val Ile Pro Glu Ala Asn Ile Pro Phe Lys Glu Ser Glu Gln Ala Ala
            100                 105                 110

Ile Val Lys Tyr Val Lys Gln Gly Gly Asn Val Val Phe Ile Ser Asp
        115                 120                 125

His Tyr Asn Ala Asp Arg Asn Leu Asn Arg Ile Asp Ser Ser Glu Ala
    130                 135                 140

Met Asn Gly Tyr Arg Arg Gly Ala Tyr Glu Asp Met Ser Lys Gly Met
145                 150                 155                 160

Asn Ala Glu Glu Lys Ser Ser Thr Ala Met Gln Gly Val Lys Ser Ser
                165                 170                 175

Asp Trp Leu Ser Thr Asn Phe Gly Val Arg Phe Arg Tyr Asn Ala Leu
            180                 185                 190

Gly Asp Leu Asn Thr Ser Asn Ile Val Ser Ser Lys Glu Ser Phe Gly
        195                 200                 205

Ile Thr Glu Gly Val Lys Ser Val Ser Met His Ala Gly Ser Thr Leu
    210                 215                 220

Ala Ile Thr Asn Pro Glu Lys Ala Lys Gly Ile Val Tyr Thr Pro Glu
225                 230                 235                 240

Gln Leu Pro Ala Lys Ser Lys Trp Ser His Ala Val Asp Gln Gly Ile
                245                 250                 255

Tyr Asn Gly Gly Gly Lys Ala Glu Gly Pro Tyr Val Ala Ile Ser Lys
            260                 265                 270

Val Gly Lys Gly Lys Ala Ala Phe Ile Gly Asp Ser Ser Leu Val Glu
        275                 280                 285

Asp Ser Ser Pro Lys Tyr Val Arg Glu Asp Asn Gly Glu Lys Lys Lys
    290                 295                 300

Thr Tyr Asp Gly Phe Lys Glu Gln Asp Asn Gly Lys Leu Leu Asn Asn
305                 310                 315                 320

Ile Thr Ala Trp Met Ser Lys Asp Asn Asp Gly Lys Ser Leu Lys Ala
                325                 330                 335

Ser Ser Leu Thr Leu Asp Thr Lys Thr Lys Leu Leu Asp Phe Glu Arg
            340                 345                 350
```

```
Pro Glu Arg Ser Thr Glu Pro Glu Lys Glu Pro Trp Ser Gln Pro Pro
        355                 360                 365

Ser Gly Tyr Lys Trp Tyr Asp Pro Thr Thr Phe Lys Ala Gly Ser Tyr
    370                 375                 380

Gly Ser Glu Lys Gly Ala Asp Pro Gln Pro Asn Thr Pro Asp Asp His
385                 390                 395                 400

Thr Pro Pro Asn Gln Asn Glu Lys Val Thr Phe Asp Ile Pro Gln Asn
            405                 410                 415

Val Ser Val Asn Glu Pro Phe Glu Met Thr Ile His Leu Lys Gly Phe
        420                 425                 430

Glu Ala Asn Gln Thr Leu Glu Asn Leu Arg Val Gly Ile Tyr Lys Glu
        435                 440                 445

Gly Gly Arg Gln Ile Gly Gln Phe Ser Ser Lys Asp Asn Asp Tyr Asn
    450                 455                 460

Pro Pro Gly Tyr Ser Thr Leu Pro Thr Val Lys Ala Asp Glu Asn Gly
465                 470                 475                 480

Asn Val Thr Ile Lys Val Asn Ala Lys Val Leu Glu Ser Met Glu Gly
            485                 490                 495

Ser Lys Ile Arg Leu Lys Leu Gly Asp Lys Thr Leu Ile Thr Thr Asp
        500                 505                 510

Phe Lys

<210> SEQ ID NO 8
<211> LENGTH: 1545
<212> TYPE: DNA
<213> ORGANISM: Staphylococcus aureus (Strain COL)

<400> SEQUENCE: 8
atgaaaaaaa tatataagtc attaactgtc tctgcaattg ttgcaacggt atcattaagt      60
gctttaccgc aatctttagc tataacgcat gaatcgcaac ctacaaagca acagcgaacg     120
gtattattcg atcgttctca tggtcaaaca gctggtgctg cagattgggt tagtgatggt     180
gcattttcag attatgcgga ttcaatacaa aaacaaggtt atgacgttaa agctattgat     240
ggtcattcga acataacaga agcaagtttg aaaagttcca aatatttgt aattcctgag     300
gctaacattc ctttcaaaga atcagaacag gcagcaattg ttaaatatgt gaaacaaggt     360
ggcaatgttg tctttatttc agatcattac aatgctgacc gaaatttaaa tcgtattgat     420
tcatcggagg caatgaatgg ttatcgacgt ggagcatatg aagatatgtc gaaaggtatg     480
aatgcagaag aaaaaagttc tactgcaatg caaggtgtga aagttcaga ttggttatct     540
acaaactttg gcgtacgttt tcgatataat gcactaggtg atttaaatac gagcaatatt     600
gtttcttcaa agaaagtttt cggtattact gaaggtgtga atctgtctc tatgcatgcc     660
ggatcgacat tagcaattac taatccagag aaagcaaaag gtattgtgta tacaccagaa     720
caattgccag cgaaaagtaa atggtcacat gctgtagatc aaggtattta atgggggc      780
ggtaaagcag aaggccccta tgtagcaatt tctaaagttg aaaaggtaa agcagcattt     840
atcggtgatt catcacttgt ggaagatagt tcgcccaaat atgtaagaga gataatgga     900
gaaaagaaga aaacatatga tggttttaaa gaacaagaca acggtaagct attaaataat     960
ataacggctt ggatgtctaa agataatgat gggaaatcac ttaaggcgag tagcctaaca    1020
ttagatacaa agactaagtt gcttgatttt gaacgaccag agcgttcaac tgagcctgaa    1080
aaagagccat ggtcacaacc gccgagtggt tataaatggt atgatccaac aacatttaaa    1140
gcaggtagtt atggcagcga aaaaggcgca gatcctcagc caaacacacc agatgatcat    1200
```

```
acaccaccaa atcagaacga aaaagtaaca tttgatatcc cgcaaaatgt ttctgtaaat    1260
gagccatttg aaatgacaat acatttaaaa ggatttgaag caaatcaaac acttgaaaat    1320
cttagagttg gtatttacaa agaaggcgga cgtcaaatcg acaattttc aagtaaagat     1380 aacgattata acccaccagg ttacagtact ttgccaacag ttaaagcaga tgaaaacgga    1440
aatgtcacaa ttaaggtcaa tgctaaagta cttgaaagta tggaaggttc aaagattcgt    1500
ttaaaactcg gtgacaaaac cttgattaca acagacttca aataa                   1545
```

```
<210> SEQ ID NO 9
<211> LENGTH: 514
<212> TYPE: PRT
<213> ORGANISM: Staphylococcus aureus (Strain Mu50)

<400> SEQUENCE: 9

Met Lys Lys Ile Tyr Lys Ser Leu Thr Val Ser Ala Ile Val Ala Thr
1               5                   10                  15

Val Ser Leu Ser Ala Leu Pro Gln Ser Leu Ala Ile Thr His Glu Ser
                20                  25                  30

Gln Pro Thr Lys Gln Gln Arg Thr Val Leu Phe Asp Arg Ser His Gly
            35                  40                  45

Gln Thr Ala Gly Ala Ala Asp Trp Val Ser Asp Gly Ala Phe Ser Asp
        50                  55                  60

Tyr Ala Asp Ser Ile Gln Lys Gln Gly Tyr Asp Val Lys Ala Ile Asp
65                  70                  75                  80

Gly His Ser Asn Ile Thr Glu Ala Ser Leu Lys Ser Ser Lys Ile Phe
                85                  90                  95

Val Ile Pro Glu Ala Asn Ile Pro Phe Lys Glu Ser Glu Gln Ala Ala
            100                 105                 110

Ile Val Asn Tyr Val Lys Gln Gly Gly Asn Val Val Phe Ile Ser Asp
        115                 120                 125

His Tyr Asn Ala Asp Arg Asn Leu Asn Arg Ile Asp Ser Ser Glu Ala
    130                 135                 140

Met Asn Gly Tyr Arg Arg Gly Ala Tyr Glu Asp Met Ser Lys Gly Met
145                 150                 155                 160

Asn Ala Glu Glu Lys Ser Ser Thr Ala Met Gln Gly Val Lys Ser Ser
                165                 170                 175

Asp Trp Leu Ser Thr Asn Phe Gly Val Arg Phe Arg Tyr Asn Ala Leu
            180                 185                 190

Gly Asp Leu Asn Thr Ser Asn Ile Val Ser Ser Lys Glu Ser Phe Gly
        195                 200                 205

Ile Thr Glu Gly Val Lys Ser Val Ser Met His Ala Gly Ser Thr Leu
    210                 215                 220

Ala Ile Thr Asn Pro Glu Lys Ala Lys Gly Ile Val Tyr Thr Pro Glu
225                 230                 235                 240

Gln Leu Pro Ala Lys Ser Lys Trp Ser His Ala Val Asp Gln Gly Ile
                245                 250                 255

Tyr Asn Gly Gly Gly Lys Ala Glu Gly Pro Tyr Val Ala Ile Ser Lys
            260                 265                 270

Val Gly Lys Gly Lys Ala Ala Phe Ile Gly Asp Ser Ser Leu Val Glu
        275                 280                 285

Asp Ser Ser Pro Lys Tyr Val Arg Glu Asp Asn Gly Glu Lys Lys Lys
    290                 295                 300

Thr Tyr Asp Gly Phe Lys Glu Gln Asp Asn Gly Lys Leu Leu Asn Asn
305                 310                 315                 320
```

Ile Thr Ala Trp Met Ser Lys Asp Ser Asp Gly Lys Ser Leu Lys Ala
            325                 330                 335

Ser Gly Leu Thr Leu Asp Thr Lys Thr Lys Leu Leu Asp Phe Glu Arg
            340                 345                 350

Pro Glu Arg Ser Thr Glu Pro Glu Lys Glu Pro Trp Ser Gln Pro Pro
            355                 360                 365

Ser Gly Tyr Lys Trp Tyr Asp Pro Thr Thr Phe Lys Ala Gly Ser Tyr
        370                 375                 380

Gly Ser Glu Lys Gly Ala Asp Pro Gln Pro Asn Thr Pro Asp Asp His
385                 390                 395                 400

Thr Pro Pro Asn Gln Asn Val Lys Ile Ser Phe Asp Ile Pro Gln Asn
            405                 410                 415

Val Ser Val Asn Glu Pro Phe Glu Val Thr Ile His Leu Lys Gly Phe
            420                 425                 430

Glu Ala Asn Gln Thr Leu Glu Asn Leu Arg Val Gly Ile Tyr Lys Glu
            435                 440                 445

Gly Gly Arg Gln Ile Gly Gln Phe Ser Ser Lys Asp Asn Asp Tyr Asn
        450                 455                 460

Pro Pro Gly Tyr Ser Thr Leu Pro Thr Val Lys Ala Asp Glu Asn Gly
465                 470                 475                 480

Asn Ala Thr Ile Lys Ile Asn Ala Lys Val Leu Glu Ser Met Glu Gly
            485                 490                 495

Ser Lys Ile Arg Leu Lys Leu Gly Asp Lys Thr Leu Ile Thr Thr Asp
            500                 505                 510

Phe Lys

<210> SEQ ID NO 10
<211> LENGTH: 1545
<212> TYPE: DNA
<213> ORGANISM: Staphylococcus aureus (Strain Mu50)

<400> SEQUENCE: 10
atgaaaaaaa tatataagtc attaactgtc tctgcaattg ttgcaacggt atcattaagt      60
gctttaccgc aatctttagc tataacgcat gaatcgcaac ctacaaagca acagcgaacg     120
gtattattcg atcgttctca tggtcaaaca gctggtgctg cagattgggt tagtgatggt     180
gcattttcag attatgcgga ttcaatacaa aaacaaggtt atgacgttaa agctattgat     240
ggtcattcga cataacagaa gcaagtttga aaagttcca aatatttgt aattcctgag      300 gctaacattc ctttcaaaga atcagaacag gcagcaattg ttaactatgt gaaacaaggt     360
ggcaatgttg tctttatttc agatcattac aatgctgacc gaaatttaaa tcgtattgat     420
tcatcggagg caatgaatgg ttatcgacgt ggagcatatg aagatatgtc gaaaggtatg     480
aatgcagaag aaaaaagctc tactgcaatg caaggtgtga aagttcaga ttggttatct       540 acaaactttg gcgtacgttt tcgatataat gcactaggtg atttaaatac gagcaatatt     600
gtttcttcaa agaaagtttt cggtattact gaaggtgtga atctgtctc tatgcatgcc      660 ggatcgacat tagcaattac taatccagag aaagcaaaag gtattgtgta tacaccagaa     720
caattgccag cgaaaagtaa atggtcacat gctgtagatc aaggtattta taatggtggc     780
ggtaaagcag aaggcccta tgtagcaatt tctaaagttg aaaaggtaa agcagcattt        840 atcggtgatt catcacttgt ggaagatagt tcgcccaaat atgtaagaga agataatgga     900
gaaaagaaga aacatatga tggttttaaa gaacaagaca acggtaagct attaaataat     960
ataacggctt ggatgtctaa agatagtgat gggaaatcac ttaaggcgag tggactaaca    1020

```
ttagatacaa agactaagtt gcttgatttt gaacgaccag agcgttcaac tgagcctgaa   1080
aaagagccat ggtcacaacc gccgagtggt tataaatggt atgacccaac acatttaaa    1140 gcaggtagtt atggcagtga aaaaggcgcg gatcctcagc caaacacacc agatgatcat   1200
acgccaccaa atcagaacgt aaaaatatca tttgatatcc cgcaaaatgt ttctgtaaat   1260
gagccatttg aagtgacaat acatttaaaa ggatttgaag caaatcaaac acttgaaaat   1320
cttagagttg gtatttacaa agaaggcgga cgtcaaatcg acaattttc aagtaaagat    1380 aacgattata acccaccagg ttacagtact ttgccaacag ttaaagcaga tgaaaacgga   1440
aatgctacaa ttaagatcaa tgctaaagta cttgaaagta tggaaggttc aaagattcgt   1500
ttaaaactcg gtgacaaaac cttgattaca acagacttca aataa                  1545
```

<210> SEQ ID NO 11
<211> LENGTH: 514
<212> TYPE: PRT
<213> ORGANISM: Staphylococcus aureus (Strain MRSA252)

<400> SEQUENCE: 11

```
Met Lys Asn Ile Tyr Lys Ser Leu Thr Val Ser Ala Ile Val Ala Thr
1               5                   10                  15

Val Ser Leu Ser Ala Leu Pro Gln Ser Leu Ala Ile Thr His Glu Ser
            20                  25                  30

Gln Pro Thr Lys Gln Gln Thr Val Leu Phe Asp Arg Ser His Gly
        35                  40                  45

Gln Thr Ala Gly Ala Ala Asp Trp Val Ser Asp Gly Ala Phe Ser Asp
    50                  55                  60

Tyr Ala Asp Ser Ile Gln Lys Gln Gly Tyr Asp Val Lys Ala Ile Asp
65                  70                  75                  80

Gly His Ser Asn Ile Thr Glu Ala Ser Leu Lys Ser Lys Ile Phe
                85                  90                  95

Val Ile Pro Glu Ala Asn Ile Pro Phe Lys Glu Ser Glu Gln Ala Ala
            100                 105                 110

Ile Val Asn Tyr Val Lys Gln Gly Gly Asn Val Phe Ile Ser Asp
        115                 120                 125

His Tyr Asn Ala Asp Arg Asn Leu Asn Arg Ile Asp Ser Ser Glu Ala
    130                 135                 140

Met Asn Gly Tyr Arg Arg Gly Ala Tyr Glu Asp Met Ser Lys Gly Met
145                 150                 155                 160

Asn Ala Glu Glu Lys Ser Ser Thr Ala Met Gln Gly Val Lys Ser Ser
                165                 170                 175

Asp Trp Leu Ser Thr Asn Phe Gly Val Arg Phe Arg Tyr Asn Ala Leu
            180                 185                 190

Gly Asp Leu Asn Thr Ser Asn Ile Val Ser Ser Lys Glu Ser Phe Gly
        195                 200                 205

Ile Thr Glu Gly Val Lys Ser Val Ser Met His Ala Gly Ser Thr Leu
    210                 215                 220

Ala Ile Thr Asn Pro Glu Lys Ala Lys Gly Ile Val Tyr Thr Pro Glu
225                 230                 235                 240

Gln Leu Pro Ala Lys Ser Lys Trp Ser His Ala Val Asp Gln Gly Ile
                245                 250                 255

Tyr Asn Gly Gly Gly Lys Ala Glu Gly Pro Tyr Val Ala Ile Ser Lys
            260                 265                 270

Val Gly Lys Gly Lys Ala Ala Phe Ile Gly Asp Ser Ser Leu Val Glu
        275                 280                 285
```

```
Asp Ser Ser Pro Lys Tyr Val Arg Glu Asp Asn Gly Glu Lys Lys Lys
    290                 295                 300

Thr Tyr Asp Gly Phe Lys Glu Gln Asp Asn Gly Lys Leu Leu Asn Asn
305                 310                 315                 320

Ile Thr Ala Trp Met Ser Lys Asp Asn Asp Gly Lys Ser Leu Lys Ala
                325                 330                 335

Ser Gly Leu Thr Leu Asp Thr Lys Thr Lys Leu Leu Asp Phe Glu Arg
            340                 345                 350

Pro Glu Arg Ser Thr Glu Pro Glu Lys Glu Pro Trp Ser Gln Pro Pro
        355                 360                 365

Ser Gly Tyr Lys Trp Tyr Asp Pro Thr Thr Phe Lys Ala Gly Ser Tyr
    370                 375                 380

Gly Ser Glu Lys Gly Ala Asp Pro Gln Pro Asn Thr Pro Asp Asp His
385                 390                 395                 400

Thr Pro Pro Asn Gln Thr Glu Lys Val Ser Phe Asp Ile Pro Gln Asn
                405                 410                 415

Val Ser Val Asn Glu Pro Phe Glu Val Thr Ile His Leu Lys Gly Phe
            420                 425                 430

Glu Ala Asn Gln Thr Leu Glu Asn Leu Arg Val Gly Ile Tyr Lys Glu
        435                 440                 445

Gly Gly Arg Gln Ile Gly Gln Phe Ser Ser Lys Asp Asn Asp Tyr Asn
    450                 455                 460

Pro Pro Gly Tyr Ser Thr Leu Pro Thr Val Lys Ala Asp Glu Asn Gly
465                 470                 475                 480

Asn Ala Thr Ile Lys Val Asn Ala Lys Val Leu Glu Ser Met Glu Gly
                485                 490                 495

Ser Lys Ile Arg Leu Lys Leu Gly Asp Lys Thr Leu Ile Thr Thr Asp
            500                 505                 510

Phe Lys

<210> SEQ ID NO 12
<211> LENGTH: 1545
<212> TYPE: DNA
<213> ORGANISM: Staphylococcus aureus (Strain MRSA252)

<400> SEQUENCE: 12
atgaaaaata tatataagtc attaactgtc tctgcaattg ttgcaacggt atcattaagt      60
gctttaccgc aatctttagc tataacgcat gaatcgcaac ctacaaagca acagcaaaca     120
gtattattcg atcgttctca tggtcaaaca gctggtgctg cagattgggt tagtgatggt     180
gcattttcag attatgcgga ttcaatacaa aaacaaggtt atgacgttaa agctattgat     240
ggtcattcga acataacaga agcaagtttg aaaagttcca aaatatttgt aattcctgag     300
gctaacattc ctttcaaaga atcagaacag gcagcaattg ttaactatgt gaaacaaggg     360
ggaaatgttg tctttatttc agaccattac aatgctgacc gaaatttaaa tcgtattgat     420
tcatcagagg caatgaatgg ttatcgacgt ggagcgtatg aagatatgtc gaaaggtatg     480
aatgcagaag aaaaaagttc tactgcaatg caaggtgtga aagttcaga ttggttatct     540 acaaactttg gcgtacgttt tcgatataat gcactaggtg atttaaatac gagcaatatt     600
gtttcttcaa agaaagtttt ggtattact gaaggtgtga atctgtatc tatgcatgcc     660 ggttcgacat tagcaattac taatccagag aaagcaaaag gtattgtgta tacaccagaa     720
caattgccac gaaaagtaa atggtcacat gctgtagatc aaggtattta taatggggc     780 ggtaaagcag aaggtcccta tgtagcaatt tctaaagttg gaaaaggtaa agcagcattt     840
```

-continued

```
atcggtgatt catcacttgt ggaagatagt tcgcccaaat atgtgagaga agataatgga    900
gaaaagaaga aaacatatga tggttttaaa gaacaagaca acggtaagct attaaataat    960
ataacagctt ggatgtctaa agataatgat gggaaatcac ttaaggcgag tggcctaaca   1020
ttagatacaa agactaagtt gcttgatttt gaacgaccag agcgttcaac tgagcctgaa   1080
aaagagccat ggtcacaacc gccgagtggt tataaatggt atgacccaac aacatttaaa   1140
gcaggtagtt atggcagtga aaaaggcgcg gatcctcagc caaacacacc agatgatcat   1200
acgccaccaa atcagaccga aaaagtatca tttgatatcc cgcaaaatgt ttctgtaaat   1260
gagccatttg aagtgacaat acatttaaaa ggatttgaag caaatcaaac acttgaaaat   1320
cttagagttg gtatttacaa agaaggagga cgtcaaatcg gacaattttc aagtaaagat   1380
aacgattata acccgccagg ttacagtact ttgccaacag ttaaagcaga tgaaaacgga   1440
aatgccacaa ttaaggtcaa tgccaaagta ctcgaaagta tggaaggttc aaagattcgt   1500
ttaaaactcg gtgacaaaac cttgattaca acagacttca aataa                   1545
```